(12) United States Patent
Jin et al.

(10) Patent No.: US 10,392,625 B2
(45) Date of Patent: Aug. 27, 2019

(54) HOST CELLS AND METHODS OF USE

(75) Inventors: Yong Hwan Jin, King of Prussia, PA (US); James D. Jowett, King of Prussia, PA (US); Alexander H. Taylor, King of Prussia, PA (US); Yuan Zhu, King of Prussia, PA (US)

(73) Assignee: GlaxoSmithKline LLC, Wilmington, DE (US)

(*) Notice: Subject to any disclaimer, the term of this patent is extended or adjusted under 35 U.S.C. 154(b) by 690 days.

(21) Appl. No.: 13/203,056

(22) PCT Filed: Feb. 24, 2010

(86) PCT No.: PCT/US2010/025223
§ 371 (c)(1),
(2), (4) Date: Aug. 24, 2011

(87) PCT Pub. No.: WO2010/099195
PCT Pub. Date: Sep. 2, 2010

(65) Prior Publication Data
US 2012/0142895 A1 Jun. 7, 2012

Related U.S. Application Data

(60) Provisional application No. 61/155,706, filed on Feb. 26, 2009.

(51) Int. Cl.
| | | |
|---|---|---|
| *C07K 14/00* | (2006.01) | |
| *C12N 15/81* | (2006.01) | |
| *C07K 14/605* | (2006.01) | |
| *C12N 9/10* | (2006.01) | |
| *C12N 9/60* | (2006.01) | |

(52) U.S. Cl.
CPC .......... *C12N 15/815* (2013.01); *C07K 14/605* (2013.01); *C12N 9/1051* (2013.01); *C12N 9/60* (2013.01); *C07K 2319/31* (2013.01)

(58) Field of Classification Search
None
See application file for complete search history.

(56) References Cited

U.S. PATENT DOCUMENTS

| 6,051,419 A | 4/2000 | Gleeson et al. |
| 6,153,424 A | 11/2000 | Raymond et al. |

FOREIGN PATENT DOCUMENTS

| WO | WO 1999/014347 | 3/1999 |

OTHER PUBLICATIONS

Macauley-Patrick et L. (Yeast, vol. 22, pp. 249-270, 2005).*
Cregg et al. (Biotech., 1993, vol. 11(8), pp. 905-910).*
Cereghino et al. (FEMS Microbiology Reviews, vol. 24, 2000, pp. 45-66).*
Gaynor, et al., J. Cell. Biol., vol. 136(4), pp. 789-802 (1997).
Gereghino, et al., FEMS Microbiol. Rev. 24(1):45-66; p. 49, col. 2, Last prargraph; Fig. 2, p. 50, col. 1 (2000).
Daly, R., et al., Expression of Heterologous Proteins in Pichia Pastoris: A Usseful Experimental Tool in Protein Engineering and Production., Journal of Molecular Recognition, vol. 18, No. 2, Mar. 1, 2005, pp. 119-138.
De Schutter, Kristof, et al: "Genome sequence of the recombinant protein production host Pichia pastoris", Nature Biotechnology, vol. 27, No. 6, Jun. 1, 2009, pp. 561-566.
Gleeson, M. A. G., et al., Genertion of Protease-Deficient Strains and Ther Use in Heterologus Protein Expression., Methods in Molecular Biology, vol. 103, Jan. 1, 1998, pp. 81-94.
Gornhardt, Birgit et al: "Cyst Germination Proteins of the Potato pathogen phytophthora infestans share homology with human mucins", Molecular Plant-Microbe Interactions, vol. 13, No. 1, Jan. 1, 2000, pp. 32-42.
Database UniProtKB/TrEMBL [Online] Feb. 10, 2009 (Feb. 10, 2009), Birren B.W.: "Predicted protein from Aspergillus terreus (strain NIH 2624)", XP002741314, Database accession No. QOC8U5 ASPTN * the whole document *.
Database UniProt [Online] Jul. 7, 2009 (Jul. 7, 2009), "SubName: Full=Pichia pastoris GS115 chromosome 2, complete sequence {ECO:0000313:EMBL:CAY68779.1};", XP002741315, retrieved from EBI accession No. Uniprot:C4QZV5 Database accession No. C4QZV5 * abstract; sequence *.

* cited by examiner

*Primary Examiner* — Hope A Robinson
(74) *Attorney, Agent, or Firm* — William T. Han; Edward R. Gimmi

(57) ABSTRACT

The present invention provides genetically modified *Pichia* strains wherein at least one nucleic acid sequence encoding a functional gene product and/or at least one nucleic acid sequence necessary for expression of at least one functional gene product in said *Pichia* strain is genetically modified, wherein said gene product is responsible for proteolysis and/or glycosylation in said genetically modified *Pichia* strain. In particular, *Pichia* strains are provided wherein nucleic acid sequence encoding a functional gene product or expression of said gene product are genetically modified: PEP4, PRB1, YPS1, YPS2, YMP1, YMP2, YMP3 and PMT4. Also provided herein are genetically modified host cells wherein wild type parent of said genetically modified host cell comprises a gene encoding a polypeptide having at least 60% sequence identity to amino acids 1-865 of SEQ ID NO:4, SEQ ID NO:6 and SEQ ID NO:8 wherein said gene is genetically modified in the genome of said host cell such that the gene product is reduced or eliminated in said genetically modified host cell compared with said wild type host cell.

2 Claims, 11 Drawing Sheets
Specification includes a Sequence Listing.

FIG 1

Novel *Pichia* protease (Ymp1) identified using affinity purification and LC/MS analysis

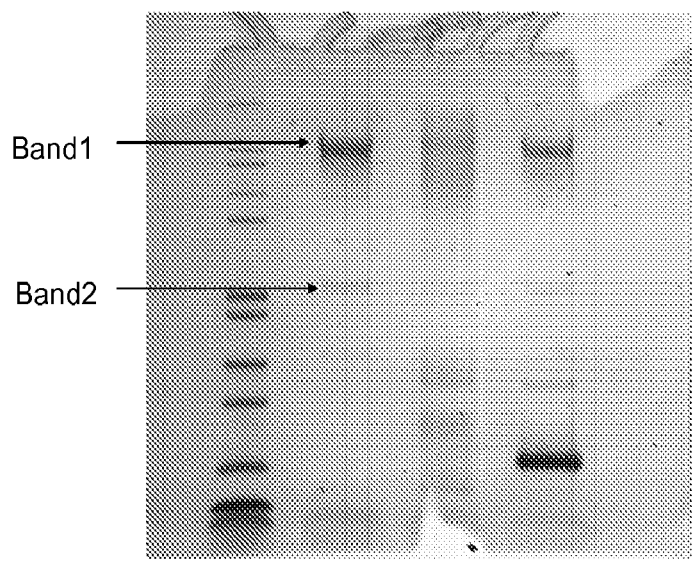

Bands 1 and 2 were excised from the gel, reduced, alkylated and digested with trypsin *in situ*. The tryptic peptides from each band were analyzed by liquid chromatography-tandem mass spectrometry. Un-interpreted sequence data were searched against the Pichia contig-peptide database using Mascot protein identification software.

FIG 2

Predicted structure of YMP1 (SEQ ID NO:4)

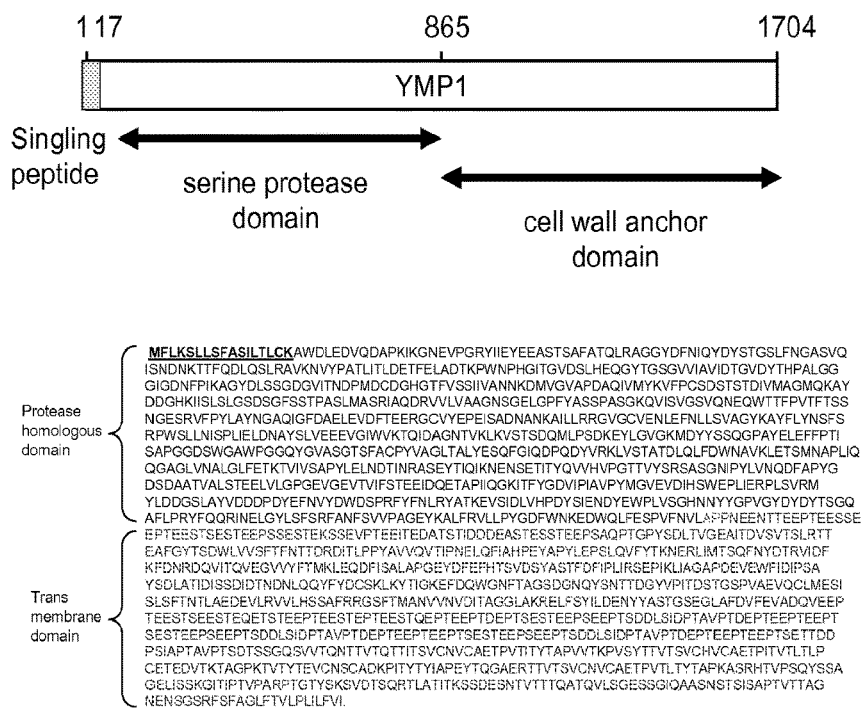

MFLKSLLSFA SILTLCKAWD LEDVQDAPKI KGNEVPGRYI IEYEEASTSA FATQLRAGGY
DFNIQYDYST GSLFNGASVQ ISNDNKTTFQ DLQSLRAVKN VYPATLITLD ETFELADTKP
WNPHGITGVD SLHEQGYTGS GVVIAVIDTG VDYTHPALGG GIGDNFPIKA GYDLSSGDGV
ITNDPMDCDG HGTFVSSIIV ANNKDMVGVA PDAQIVMYKV FPCSDSTSTD IVMAGMQKAY
DDGHKIISLS LGSDSGFSST PASLMASRIA QDRVVLVAAG NSGELGPFYA SSPASGKQVI
SVGSVQNEQW TTFPVTFTSS NGESRVFPYL AYNGAQIGFD AELEVDFTEE RGCVYEPEIS
ADNANKAILL RRGVGCVENL EFNLLSVAGY KAYFLYNSFS RPWSLLNISP LIELDNAYSL
VEEEVGIWVK TQIDAGNTVK LKVSTSDQML PSDKEYLGVG KMDYYSSQGP AYELEFFPTI
SAPGGDSWGA WPGGQYGVAS GTSFACPYVA GLTALYESQF GIQDPQDYVR KLVSTATDLQ
LFDWNAVKLE TSMNAPLIQQ GAGLVNALGL FETKTVIVSA PYLELNDTIN RASEYTIQIK
NENSETITYQ VVHVPGTTVY SRSASGNIPY LVNQDFAPYG DSDAATVALS TEELVLGPGE
VGEVTVIFST EEIDQETAPI IQGKITFYGD VIPIAVPYMG VEVDIHSWEP LIERPLSVRM
YLDDGSLAYV DDDPDYEFNV YDWDSPRFYF NLRYATKEVS IDLVHPDYSI ENDYEWPLVS
GHNNYYGPVG YDYDYTSGQA FLPRYFQQRI NELGYLSFSR FANFSVVPAG EYKALFRVLL
PYGDFWNKED WQLFESPVFN VLAPP (SEQ ID NO: 15)

Protease activity assay of *ymp1* mutant strain

B580 and B581 were fermentation batches for SMD1163_*ymp1*
B589 was fermentation batch for control strain SMD1163

FIG 4
Zymogram analysis of *ymp1* mutant strain
10% Zymogram – Gelatin
1  2  3  4
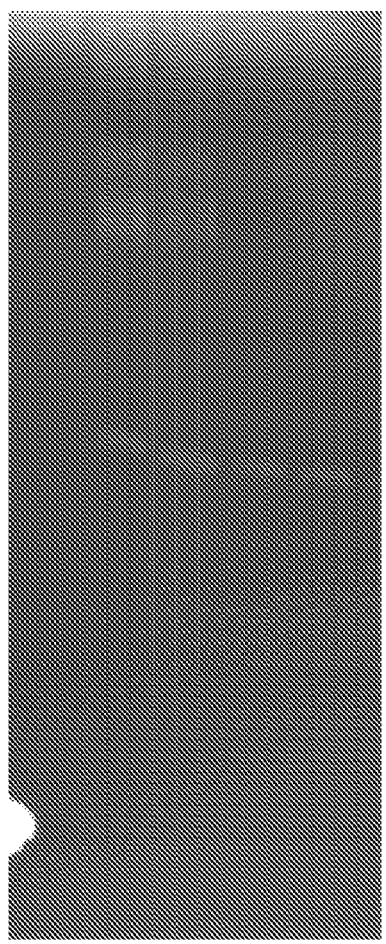
12% Zymogram - Casein
1  2  3  4
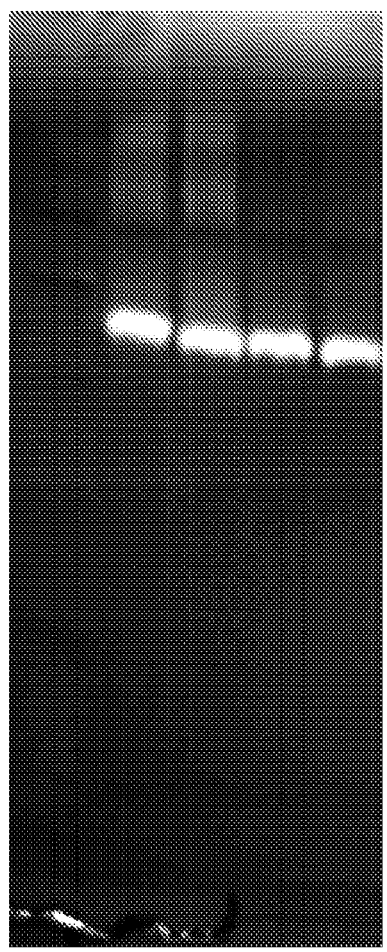
Sample 1 – SMD1163
Sample 2 – X33_*pep4*
Sample 3 – SMD1163_*ymp1*_clone 1
Sample 4 – SMD 1163_*ymp1*_clone 2

*ymp1* knockout effect on proteolysis of heterologous protein (SED ID NO:1)

1. See Blue Plus 2
2. Seq ID No:1 Std.
3. B563 *ymp1* KO 118.2 hr
4. B564 *pmt4* KO 118.7 hr
5. B565 *pmt4* KO 118.7 hr

*ysp2* Knockout Effect on Proteolysis of Heterologous Protein (SED ID NO:1)

1-See Blue Plus 2
2-SEQ ID NO:1 Std.
3-B542 125 hr
4-B542 148 hr
5-B542 169 hr
6-B544 125 hr
7-B544 148 hr
8-B544 169 hr
9-B545 125 hr
10-B545 148 hr
11-B545 168 hr
12-SEQ ID NO:1 Std
13-Blank
14-Blank
15-See Blue Plus 2

*ysp1* Knockout Effect on Proteolysis of Heterologous Protein (SED ID NO:1)

1 – SeeBlue Plus Marker
2 – SEQ ID NO:1 std
3 – X33pep4yps1
4 – X33pep4yps1/SEQ ID NO:1
5 – X33pep4/SEQ ID NO:1

*pep4* Knockout Effect on Proteolysis of Heterologous Protein (SED ID NO:1)

1 – SEQ ID NO:1 standard
2 - GS115[SEQ ID NO:1]
3 - X33 Δpep4 [SEQ ID NO:1]]

Buffer stability study of *ymp2* and *ymp3* mutant strains

24 hour 30° C incubation

1 – PBS control
2 – SMD1163_24 hr induction
3 – SMD1163_*ymp3*_24 hr induction
4 – SMD1163_*ymp2*_24 hr induction Zymolyase Assay results for Wild Type (WT), *pmt1* and *pmt4 Pichia* mutants.

Glycosylation analysis of *pmt4* mutant strain by LC/MS

HOST CELLS AND METHODS OF USE

This application claims the benefit of U.S. Provisional Application No. 61/155,706 filed 26 Feb. 2009 which is incorporated herein in its entirety.

This application is a 371 of International Application No. PCT/US2010/025223, filed 24 Feb. 2010, which claims the benefit of U.S. Provisional Application No. 61/155,706, filed 26 Feb. 2009, which are both incorporated by reference in their entireties.

FIELD OF THE INVENTION

This invention is in the field of biochemical engineering. More particularly, this invention relates to genetically modified *Pichia* strains and methods for producing polypeptides in them.

BACKGROUND OF THE INVENTION

Therapeutic polypeptides and proteins can be expressed in a variety of host cells including bacterial cells, *E. coli* cells, fungal or yeast cells, cells of a microorganism, insect cells, and mammalian cells. Fungal hosts such as the methylotrophic yeast *Pichia pastoris* has distinct advantages for therapeutic protein expression—e.g. it does not secrete high amounts of endogenous proteins, it has a strong inducible promoter, it can be grown in defined chemical media, and it can produce high titers of recombinant proteins (Cregg et al., *Mol. Biotech.* 16:23-52 (2000)). Yeast and filamentous fungi have both been successfully used for the production of recombinant proteins, both intracellular and secreted (Cereghino, J. L. and J. M. Cregg 2000 *FEMS Microbiology Reviews* 24(1): 45 66; Harkki, A., et al. 1989 *Bio-Technology* 7(6): 596; Berka, R. M., et al. 1992 Abstr. *Papers Amer. Chem. Soc.* 203: 121-BIOT; Svetina, M., et al. 2000 *J. Biotechnol.* 76(23): 245-251. *Pichia* is a remarkable host cell for expression of recombinant human serum albumin (HSA). However, the expression of other therapeutic polypeptides including polypeptides genetically fused with HSA faces the technical barriers of undesired proteolysis and glycosylation.

Heterologous proteins expressed in *P. pastoris* may contain additional mannose sugars resulting in "high mannose" glycans, as well as mannosylphosphate groups which impart a negative charge onto a protein. Glycosylated proteins with either high mannose glycans or charged mannans are a high risk for eliciting an immune response in humans (Takeuchi, *Trends in Glycosci. & Glycotech.*, 9:S29-S35 (1997); Rosenfeld et al., *J. Biol. Chem.*, 249:2319-2321 (1974)). Accordingly, it is desirable to produce therapeutic peptides, polypeptides and/or proteins in fungal host systems, such that the pattern of glycosylation is identical or at least similar to that in humans.

Thus, there is a need for yeast strains, in particular *Pichia* strains that are capable of producing heterologous peptides, polypeptides and/or proteins with reduced proteolysis and/or glycosylation when compared with wild type strains. In addition, there is a need to identify genes within yeast strains, in particular *Pichia* strains, responsible for producing proteins involved in proteolytic and glycosylation pathways.

SUMMARY OF THE INVENTION

In one aspect of the present invention, genetically modified *Pichia* strains are provided wherein at least one nucleic acid sequence encoding a functional gene product and/or at least one nucleic acid necessary for expression of at least one gene product in said *Pichia* strain is genetically modified, wherein said gene product is responsible for proteolysis and/or glycosylation in said genetically modified *Pichia* strain.

Also provided herein are methods of producing at least one heterologous polypeptide comprising expressing said one heterologous polypeptide in a genetically modified *Pichia* strains of the present invention. In another aspect, the present invention provides heterologously expressed peptides, polypeptides, and proteins expressed in the host cells of the present invention.

In another aspect of the present invention, an isolated polypeptide having at least 50%, 55%, 60%, 65%, 70%, 75%, 80%, 85%, 90%, 95%, 99% and/or 100% sequence identity to SEQ ID NO:4, SEQ ID NO:6 and SEQ ID NO:8 are provided. Also provided are a genetically modified host cell strain wherein said wild type parent of said host cell comprises a gene encoding a polypeptide having at least 60% sequence identity to SEQ ID NOs:4, 6 and 8 wherein said gene is genetically modified in the genome of said host cell such that the gene product or its activity is reduced or eliminated in said genetically modified host cell compared with said wild type host cell.

BRIEF DESCRIPTION OF THE FIGURES

FIG. 1: Novel *Pichia* protease Ymp1 identified using affinity purification and LC/MS analysis FIG. 2: Predicted structure of YMP1 (SEQ ID NO:4) showing amino acids 1-857 as SEQ ID NO:15.

FIG. 4: Zymogram assay of ymp1 mutant strain

DETAILED DESCRIPTION OF THE INVENTION

Figure 3:
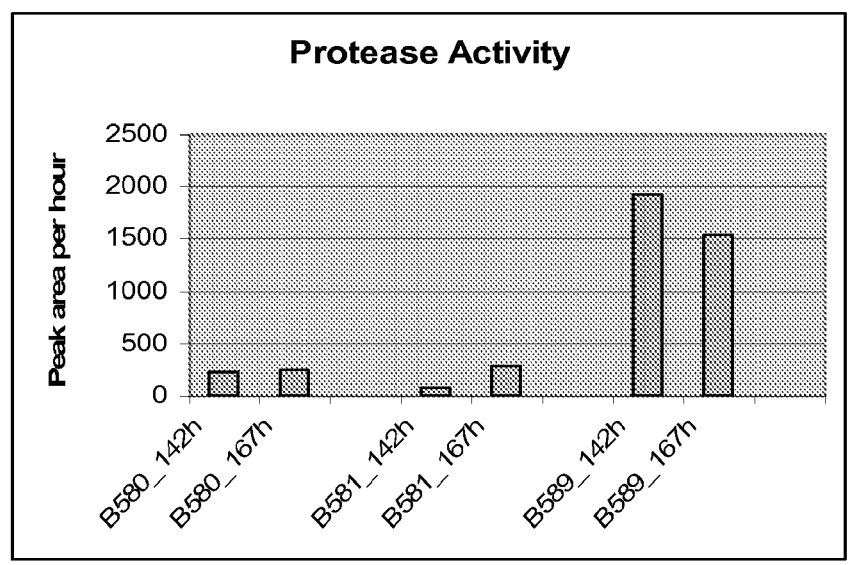
FIG. 3: Protease activity assay of ymp1 mutant strain
Figure 5:
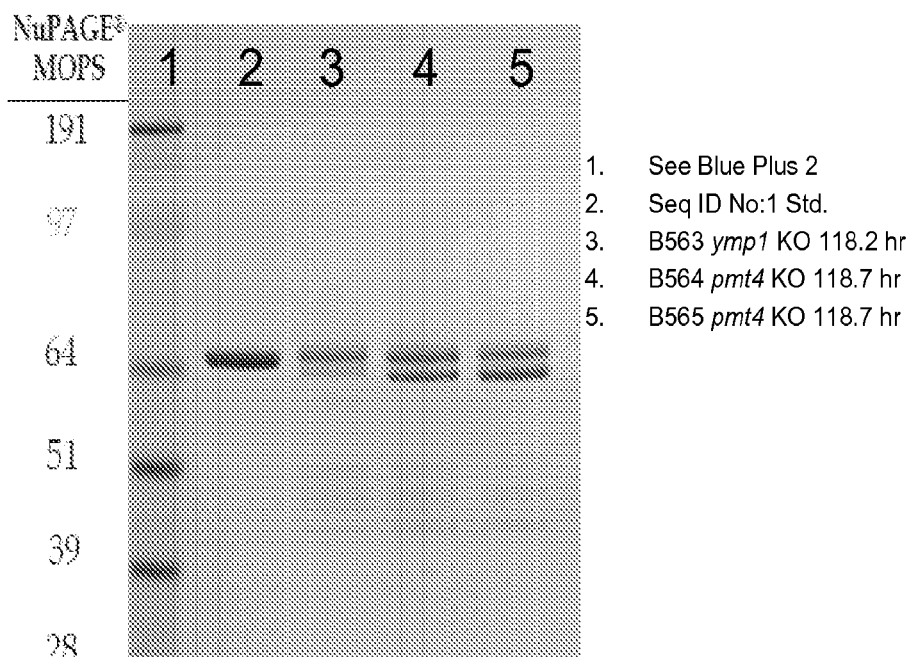
FIG. 5: ymp1 knockout effect on proteolysis of heterologous protein (SEQ ID NO:1)
Figure 6:
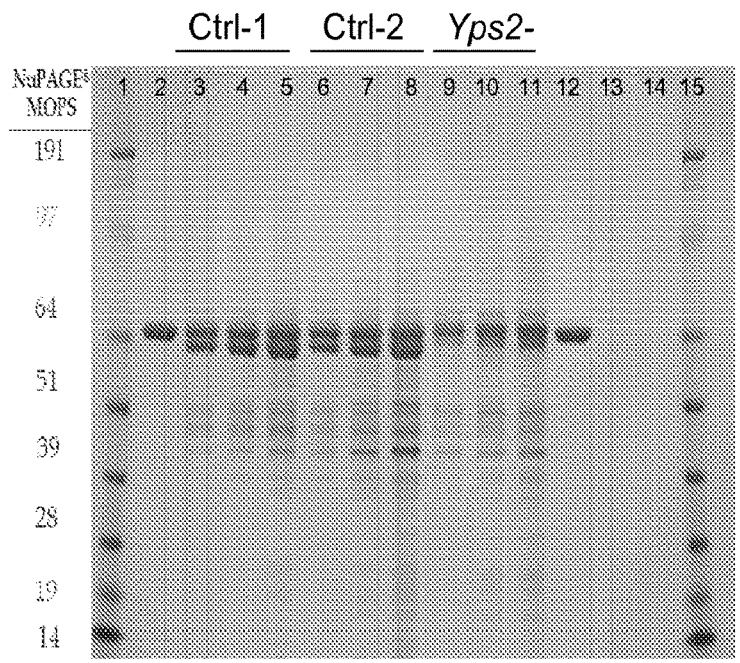
FIG. 6: ysp2 knockout effect on proteolysis of heterologous protein (SEQ ID NO:1)
Figure 7:
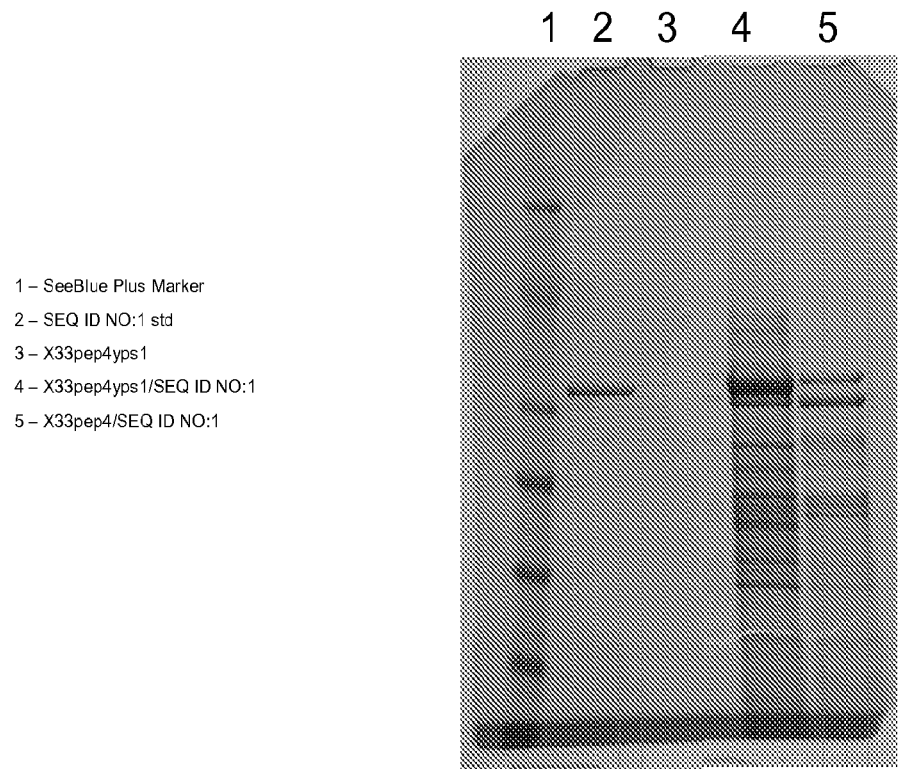
FIG. 7: ysp1 knockout effect on proteolysis of heterologous protein (SEQ ID NO:1)
Figure 8:
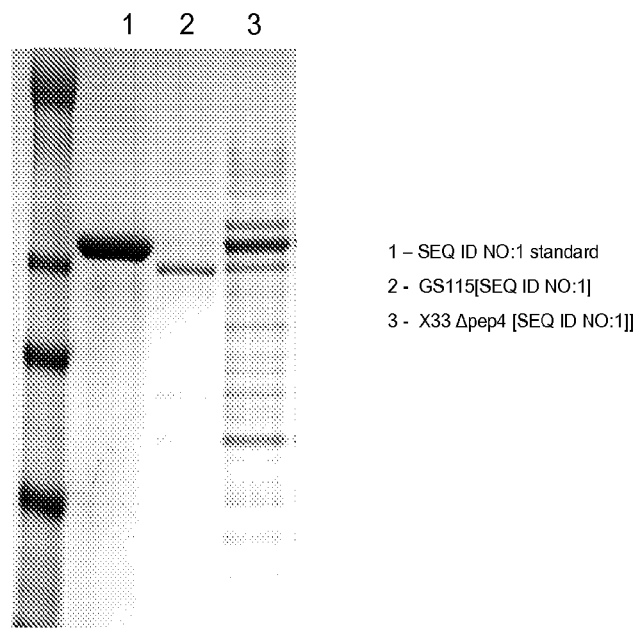
FIG. 8: pep4 knockout effect on proteolysis of heterologous protein (SEQ ID NO:1)

"Host cell(s)" as used herein refers to a cell that has been introduced (e.g., transformed, infected or transfected) or is capable of introduction (e.g., transformation, infection or transfection) by an isolated polynucleotide sequence. Host cells of the present invention may include, but are not limited to bacterial cells, fungal cells, yeast cells, a cell of a microorganism, insect cells and mammalian cells. The host cells of the present invention of yeast and/or filamentous fungal origin may include, but are not limited to, the following families, genie, and species: *Pichia pastoris, Pichia finlandica, Pichia trehalophila, Pichia koclamae, Pichia membranaefaciens, Pichia methanolica, Pichia minuta* (*Ogataea minuta, Pichia lindneri*), *Pichia opuntiae, Pichia thermotolerans, Pichi salictaria, Pichia guercum, Pichia pijperi, Pichia stiptis, Pichia* sp., *Saccharomyces*

*castelii, Saccharomyces cerevisiae, Saccharomyces kluyveri, Saccharomyces* sp., *Hansenula polymorpha, Kluyveromyces* sp., *Kluyveromyces lactis, Candida albicans, Candida* sp., *Aspergillus fumigatus, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa.*

"Transformed" as known in the art, is the directed modification of an organism's genome or episome via the introduction of external DNA or RNA, or to any other stable introduction of external DNA or RNA.

"Transfected" as known in the art, is the introduction of external DNA or RNA into a microorganism, including but not limited to recombinant DNA or RNA.

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403-410 (1990). The BLAST X program is publicly available from NCBI and other sources (BLAST Manual, Altschul, S., et al., NCBI NLM NIH Bethesda, Md. 20894; Altschul, S., et al., *J. Mol. Biol.* 215: 403-410 (1990). The well known Smith Waterman algorithm may also be used to determine identity.

Parameters for polypeptide sequence comparison include the following: Algorithm: Needleman and Wunsch, J. Mol. Biol. 48: 443-453 (1970) Comparison matrix: BLOSSUM62 from Hentikoff and Hentikoff, Proc. Natl. Acad. Sci. USA. 89:10915-10919 (1992)
Gap Penalty: 12
Gap Length Penalty: 4
A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following: Algorithm: Needleman and Wunsch, J. Mol. Biol. 48: 443-453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid comparisons.

A meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to a reference sequence, for example, SEQ ID NO:3, wherein said polynucleotide sequence may be identical to the reference sequence of SEQ ID NO:3 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:3 by the integer defining the percent identity divided by 100 and then subtracting that product from said total number of nucleotides in SEQ ID NO:3, or:

$$n_n \leq x_n - (x_n \cdot y),$$

wherein $n_n$ is the number of nucleotide alterations, $x_n$ is the total number of nucleotides in SEQ ID NO:3, y is 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding a polypeptide may create nonsense, missense or frameshift mutations in this coding sequence and thereby alter the polypeptide encoded by the polynucleotide following such alterations.

(2) Polypeptide embodiments further include an isolated polypeptide comprising a polypeptide having at least a 50, 60, 70, 80, 85, 90, 95, 97 or 100% identity to a polypeptide reference sequence, such as SEQ ID NO:4, wherein said polypeptide sequence may be identical to the reference sequence or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids by the integer defining the percent identity divided by 100 and then subtracting that product from said total number of amino acids, or:

$$n_a \leq x_a - (x_a \cdot y),$$

wherein $n_a$ is the number of amino acid alterations, $x_a$ is the total number of amino acids in the sequence, y is 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated," including, but not limited to, when such polynucleotide or polypeptide is introduced back into a cell.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence is placed adjacent to the endogenous nucleic acid sequence, such that the expression of this endogenous nucleic acid sequence is altered, for example, increased, decreased or eliminated. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site and a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein "nucleic acid sequence encoding a functional gene product" refers to any portion of an encoding part of a gene. The nucleic acid sequence encoding a functional gene product may be a portion of an enzyme that is capable of doing at least one activity of the whole enzyme or an entire enzyme.

As used herein "nucleic acid necessary for expression of at least one gene product" refers to a nucleic acid sequence that encodes any portion of a gene and/or is operably linked to a nucleic acid encoding a gene product but does not necessarily comprise encoding sequence. By way of example, a nucleic acid sequence necessary for the expression of at least one gene product includes, but is not limited to, enhancers, promoters, regulatory sequences, start codons, stop codons, polyadenylation sequences, and/or encoding sequences.

As used herein "proteolysis" or "gene product responsible for proteolysis in a cell" refers to any peptide, polypeptide, protein and/or enzyme or portion thereof capable of causing the cleavage of at least one peptide, polypeptide and/or protein. The gene product responsible for proteolysis may be directly responsible for cleavage (ie, a peptidase) or it may be indirectly responsible as part of a peptidase synthesis pathway. Examples of gene products that are responsible for proteolysis in a cell include, but are not limited to, aspartyl proteases, serine proteases, secreted aspartyl proteases, secreted serine proteases, yeast methyltrophic proteases, DPP IV like endopeptidases, metalloendopeptidases, Prb1-like serine proteases, Prb1 serine proteases, and CPY like carboxypeptidases. Also, included in this definition are protease that may be secreted from a cell, but still maintain some or all of it proteolysis activity, such as a secreted serine protease. A secreted protease may be responsible for proteolysis within the cell and/or outside the cell.

As used herein "glycosylation" or "gene product responsible for glycosylation in a cell" refers to any peptide, polypeptide, protein and/or enzyme or portion thereof involved in the addition of at least one saccharide moiety to a polypeptide or elongation of at least one saccharide chain in the cell. The gene product responsible for glycosylation in a cell may be directly responsible for the addition of a saccharide to a polypeptide in a cell, for example, but not limited to mannosyltranferases. Mannosyltransferases may transfer a residue from Dol-P-Man to a serine and/or threonine residue on a peptide, polypeptide and/or protein or may act to transfer a mannose residue from GPD-Man to a saccharide, thus, elongating the saccharide chain. Alternatively, the gene product responsible for glycosylation may be part of a glycosylation pathway and may be indirectly responsible for the addition of polysaccharide to a polypeptide in a cell. Examples of gene products that are responsible for glycosylation in a cell include, but are not limited to mannosyltranferases.

As used herein "yeast methyltropic protease 1 (Ymp1) activity" refers to any activity that the protein identified herein as SEQ ID NO:4 can perform. For example, yeast methyltrophic protease 1 activity or Ymp1 activity includes, but is not limited to, an enzyme's ability to proteolytically cleave a peptide, polypeptide, or protein. In particular, Ymp1 activity can refer to an enzyme's ability to cleave a polypeptide comprising a fragment and/or variant of a GLP-1 agonist, such as, but not limited to, human GLP-1, and/or human albumin. At least one Ymp1 activity includes, but is not limited to, at least one serine protease activity.

"Polynucleotide(s)" generally refers to any polyribonucleotide or polydeoxyribonucleotide, that may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES*, 2nd Ed., T. E. Creighton, W. H. Freeman and Company, New York (1993) and Wold, F., Posttranslational Protein Modifications: Perspectives and Prospects, pgs. 1-12 in *POSTTRANSLATIONAL COVALENT MODIFICATION OF PROTEINS*, B. C. Johnson, Ed., Academic Press, New York (1983); Seifter et al., *Meth. Enzymol.* 182:626-646 (1990) and Rattan et al., *Protein Synthesis: Posttranslational Modifications and Aging*, Ann N Y Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

"Recombinant expression system(s)" refers to expression systems or portions thereof or polynucleotides of the invention introduced, transfected or transformed into a host cell or host cell lysate for the production of the polynucleotides and polypeptides of the invention.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion proteins and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. The present invention also includes include variants of each of the polypeptides of the invention, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly there are variants in which several, 5-10, 1-5, 1-3, 1-2 or 1 amino acids are substituted, deleted, or added in any combination. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

"Microorganism(s)" means a (i) prokaryote, including but not limited to, a member of the genus *Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma*, and further including, but not limited to, a member of the species or group, Group A *Streptococcus*, Group B *Streptococcus*, Group C *Streptococcus*, Group D *Streptococcus*, Group G *Streptococcus, Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella* vaginalis, *Mycobacterium tuberculosis*, *Mycobacterium bovis*, *Mycobacterium ulcerans*, *Mycobacterium leprae*, *Actinomyctes israelii*, *Listeria monocytogenes*, *Bordetella pertusis*, *Bordatella parapertusis*, *Bordetella bronchiseptica*, *Escherichia coli*, *Shigella dysenteriae*, *Haemophilus influenzae*, *Haemophilus aegyptius*, *Haemophilus parainfluenzae*, *Haemophilus ducreyi*, *Bordetella*, *Salmonella typhi*, *Citrobacter freundii*, *Proteus mirabilis*, *Proteus vulgaris*, *Yersinia pestis*, *Kleibsiella pneumoniae*, *Serratia marcessens*, *Serratia liquefaciens*, *Vibrio cholera*, *Shigella dysenterii*, *Shigella flexneri*, *Pseudomonas aeruginosa*, *Franscisella tularensis*, *Brucella abortis*, *Bacillus anthracis*, *Bacillus cereus*, *Clostridium perfringens*, *Clostridium tetani*, *Clostridium botulinum*, *Treponema pallidum*, *Rickettsia rickettsii* and *Chlamydia trachomitis*, (ii) an archaeon, including but not limited to *Archaebacter*, and (iii) a unicellular or filamentous eukaryote, including but not limited to, a protozoan, a fungus, a member of the genus *Saccharomyces*, *Kluveromyces*, or *Candida*, and a member of the species *Saccharomyces ceriviseae*, *Kluveromyces lactis*, or *Candida albicans*.

"Bacteria(um)(1)" means a (i) prokaryote, including but not limited to, a member of the genus *Streptococcus*, *Staphylococcus*, *Bordetella*, *Corynebacterium*, *Mycobacterium*, *Neisseria*, *Haemophilus*, *Actinomycetes*, *Streptomycetes*, *Nocardia*, *Enterobacter*, *Yersinia*, *Fancisella*, *Pasturella*, *Moraxella*, *Acinetobacter*, *Erysipelothrix*, *Branhamella*, *Actinobacillus*, *Streptobacillus*, *Listeria*, *Calymmatobacterium*, *Brucella*, *Bacillus*, *Clostridium*, *Treponema*, *Escherichia*, *Salmonella*, *Kleibsiella*, *Vibrio*, *Proteus*, *Erwinia*, *Borrelia*, *Leptospira*, *Spirillum*, *Campylobacter*, *Shigella*, *Legionella*, *Pseudomonas*, *Aeromonas*, *Rickettsia*, *Chlamydia*, *Borrelia* and *Mycoplasma*, and further including, but not limited to, a member of the species or group, Group A *Streptococcus*, Group B *Streptococcus*, Group C *Streptococcus*, Group D *Streptococcus*, Group G *Streptococcus*, *Streptococcus pneumoniae*, *Streptococcus pyogenes*, *Streptococcus agalactiae*, *Streptococcus faecalis*, *Streptococcus faecium*, *Streptococcus durans*, *Neisseria gonorrheae*, *Neisseria meningitidis*, *Staphylococcus aureus*, *Staphylococcus epidermidis*, *Corynebacterium diptheriae*, *Gardnerella vaginalis*, *Mycobacterium tuberculosis*, *Mycobacterium bovis*, *Mycobacterium ulcerans*, *Mycobacterium leprae*, *Actinomyctes israelii*, *Listeria monocytogenes*, *Bordetella pertusis*, *Bordatella parapertusis*, *Bordetella bronchiseptica*, *Escherichia coli*, *Shigella dysenteriae*, *Haemophilus influenzae*, *Haemophilus aegyptius*, *Haemophilus parainfluenzae*, *Haemophilus ducreyi*, *Bordetella*, *Salmonella typhi*, *Citrobacter freundii*, *Proteus mirabilis*, *Proteus vulgaris*, *Yersinia pestis*, *Kleibsiella pneumoniae*, *Serratia marcessens*, *Serratia liquefaciens*, *Vibrio cholera*, *Shigella dysenterii*, *Shigella flexneri*, *Pseudomonas aeruginosa*, *Franscisella tularensis*, *Brucella abortis*, *Bacillus anthracis*, *Bacillus cereus*, *Clostridium perfringens*, *Clostridium tetani*, *Clostridium botulinum*, *Treponema pallidum*, *Rickettsia rickettsii* and *Chlamydia trachomitis*, and (ii) an archaeon, including but not limited to *Archaebacter*.

As used herein, "heterologous polypeptide(s)" refers to a polypeptide not naturally synthesized by a transformed host cell or microorganism of interest and introduced into the host cell or microorganism by recombinant DNA. For example, *Pichia* may act as a host cell for the expression of human serum albumin, which does not occur in non-transformed or non-transfected *Pichia*. Heterologous polypeptides may include polypeptides that have been modified to facilitate isolation.

As used herein "affinity tag" refers to any moiety associated with a molecule that may give said molecule a selective affinity for another substance or molecule. For instance, an affinity tag may be used to facilitate purification of a molecule by providing the molecule with a selective affinity for a column's packing material. A non-limiting example of an affinity tag is a his-tag.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein "harvesting" cells refers to collection of cells from cell culture. Cells may be concentrated during harvest to separate them from culture broth, for instance by centrifugation or filtration. Harvesting cells may further comprise the step of lysing the cells to obtain intracellular material, such as, but not limited to polypeptides and polynucleotides. It should be understood by the skilled artisan that certain cellular material, including but not limited to, heterologously expressed polypeptide, may be released from cells during culture. Thus, a product (e.g., a heterologously expressed polypeptide) of interest may remain in culture broth after cells are harvested.

Also, provided are methods wherein the recombinant DNA construct encodes a selectable marker. Such a selectable marker provides for either positive or negative selection. Methods are also provided comprising expressing said selectable marker and comparing the amount of selectable marker produced by at least one first transformed cell of the selecting step with the amount of selectable marker produced by at least one second transformed cell of the selecting step wherein the first and second transformed cell produce the same selectable marker. As is understood in the art, selectable markers include, but are not limited to, dihydrofolate reductase (dhfr), β-galactosidase, fluorescent protein, secreted form of human placental alkaline phosphatase, beta-glucuronidase, yeast selectable markers LEU2 and URA3, apoptosis resistant genes, and antisense oligonucleotides, as well as antibiotic resistance genes conferring the ability to grow in the presence of antibiotics including, neomycin (neo), kanamycin, geneticin, hygromycin B, puromycin, zeocin, blasticidin, nourseothricin, bialaphos, phleomycin, and ampicillin. As is also understood in the art, cells can be sorted by a variety of means, including but not limited to, visual inspection or a cell sorter such as a BD FACS Aria, which can detect expression of a selectable marker.

The term "wild type" as is understood in the art refers to a host cell or a polypeptide or polynucleotide sequence that occurs in a native population without genetic modification. For example, a "wild type parent of a host cell" refers to an unmodified strain of a host cell prior to any genetic modification being made or occurring in the genome of the host cell.

As used herein, "titer yield" refers to the concentration of a product (e.g., heterologously expressed polypeptide) in solution (e.g., culture broth or cell-lysis mixture or buffer) and it usually expressed as mg/L or g/L. An increase in titer yield may refer to an absolute or relative increase in the concentration of a product produced under two defined set of conditions.

"Incretin hormone" as used herein means any hormone that potentiates insulin secretion or otherwise raises the level or insulin. One example of an incretin hormone is GLP-1. GLP-1 is an incretin secreted by intestinal L cells in response to ingestion of food. In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying time and slows small bowel motility delaying food absorption. GLP-1 promotes continued beta cell competence by stimulating transcription of genes involved in glucose dependent insulin secretion and by promoting beta-cell neogenesis (Meier, et al. *Biodrugs* 2003; 17 (2): 93-102).

"GLP-1 activity" as used herein means one or more of the activities of naturally occurring human GLP-1, including but not limited to, reducing blood and/or plasma glucose, stimulating glucose-dependent insulin secretion or otherwise raising the level or insulin, suppressing glucagon secretion, reducing fructosamine, increases glucose delivery and metabolism to the brain, delaying gastric emptying, and promoting beta cell competence, and/or neogenesis. Any of these activities and other activity associated with GLP-1 activity may be caused directly or indirectly by a composition having GLP-1 activity or a GLP-1 agonist. By way of example, a composition having GLP-1 activity may directly or indirectly stimulate glucose-dependent while the stimulation of insulin production may indirectly reduce plasma glucose levels in a mammal An "incretin mimetic" as used herein is a compound capable of potentiating insulin secretion or otherwise raise the level or insulin. An incretin mimetic may be capable of stimulating insulin secretion, increasing beta cell neogenesis, inhibiting beta cell apoptosis, inhibiting glucagon secretion, delaying gastric emptying and inducing satiety in a mammal. An incretin mimetic may include, but is not limited to, any polypeptide which has GLP-1 activity, including but not limited to, exendin 3 and exendin 4, including any fragments and/or variants and/or conjugates thereof.

As used herein "fragment," when used in reference to a polypeptide, is a polypeptide having an amino acid sequence that is the same as part but not all of the amino acid sequence of the entire naturally occurring polypeptide. Fragments may be "free-standing" or comprised within a larger polypeptide of which they form a part or region as a single continuous region in a single larger polypeptide. By way of example, a fragment of naturally occurring GLP-1 would include amino acids 7 to 36 of naturally occurring amino acids 1 to 36. Furthermore, fragments of a polypeptide may also be variants of the naturally occurring partial sequence. For instance, a fragment of GLP-1 comprising amino acids 7-30 of naturally occurring GLP-1 may also be a variant having amino acid substitutions within its partial sequence.

As used herein "conjugate" or "conjugated" refers to two molecules that are bound to each other. For example, a first polypeptide may be covalently or non-covalently bound to a second polypeptide. The first polypeptide may be covalently bound by a chemical linker or may be genetically fused to the second polypeptide, wherein the first and second polypeptide share a common polypeptide backbone. Conjugate of the present invention may comprise at least one therapeutic polypeptide conjugated to human serum albumin. Other conjugates also include, but are not limited to, at least one therapeutic polypeptides conjugated to transferrin, a single chain variable domain, and/or at least one Fc region of an antibody. Conjugates may or may not comprise a linker.

As used herein "tandemly oriented" refers to two or more polypeptides that are adjacent to one another as part of the same molecule. They may be linked either covalently or non-covalently. Two or more tandemly oriented polypeptides may form part of the same polypeptide backbone. Tandemly oriented polypeptides may have direct or inverted orientation and/or may be separated by other amino acid sequences.

A "domain antibody" or "dAb" may be considered the same as a "single variable domain" which is capable of binding to an antigen. A single variable domain may be a human antibody variable domain, but also includes single antibody variable domains from other species such as rodent (for example, as disclosed in WO 00/29004), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanized according to standard techniques available in the art, and such domains are considered to be "domain antibodies". As used herein $V_H$ includes camelid $V_{HH}$ domains.

The phrase "single variable domain" refers to an antigen binding protein variable domain (for example, $V_H$, $V_{HH}$, $V_L$) that specifically binds an antigen or epitope independently of a different variable region or domain.

The term "antigen binding protein" as used herein refers to antibodies, antibody fragments and other protein constructs, such as domains, but not limited to, variable domains and domain antibodies, which are capable of binding to an antigen.

As used herein, "reduced amount" of an enzyme or fragment thereof or enzyme activity compared in a genetically modified host cell refers to a genetically modified host cell which produces less of at least one enzyme or shows less of at least one kind of enzyme activity when compared with a non-genetically modified host cell. Typically, the comparison in enzyme activity produced by a genetically modified host cell is with the wild type strain of the same species before genetic modification. However, the comparison can also be between genetically modified host and a wild type host from the genus but different species or strain or with another genetically modified strain. A reduction in at least one enzyme or enzyme activity also includes a complete abrogation of at least one enzyme or enzyme activity in which none of at least one enzyme is produced in a genetically modified host cell and/or none of at least one enzyme is functional or shows activity. Also included within this definition is a reduced amount of at least one enzyme activity. That is, enzymes which have more then one activity may maintain the amount of a first activity while a second activity of the same enzyme is reduced.

As herein used, the terms "stringent conditions" and a "stringent hybridization conditions" mean hybridization will occur only if there is at least 70% and at least 80%, but at least 95% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing the filters in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein, the disclosure of which is hereby incorporated in its entirety by reference.

As used herein "genetic modification" or "genetically modified" refers to any suppression, substitution, deletion and/or insertion of one or more bases or of a fragment of a cell DNA sequence(s). Such genetic modification may be obtained in vitro (directly on isolated DNA) or in situ, for example by genetic engineering techniques or by exposing the cells to a mutagenic agent. Mutagenic agents include, for example, physical agents such as energetic rays (X-rays, y-rays, UV, etc.) or chemical agents capable of reacting with different functional groups of DNA, such as alkylating agents (EMS, NQO, etc.) bialkylating agents, intercalating agents, etc. Genetic modifications may also be obtained by genetic disruption for example according to the method disclosed by Rothstein et al. (Meth. Enzymol. 194:281-301 (1991)). According to this method, part or all of a gene is replaced through homologous recombination by an in vitro modified version. Genetic modifications can also be obtained by any mutation insertion on DNA sequences, such as transposons, phages, etc. Also, as used herein "genetically modified" can refer to a gene encoding a polypeptide or a polypeptide having at least one deletion, substitution or suppression of a nucleic acid or amino acid, respectively. For example, a polypeptide in which at least one amino acid is substituted from the wild type form would be considered genetically modified.

Genetic modification may be reversed or attenuated by cellular mechanism. Alternatively, mutations can be non-reverting and or non-leaky. "Leaky mutations" include mutations that result in a partial rather than a complete inactivation of wild type function.

The genetic modifications carried by the host cells of the invention may be located in a coding region of the DNA sequence of the cell and/or in a region affecting the expression of a gene. Modifications of the invention will generally, therefore, affect gene product or regulation or promotion of gene product of proteins and/or enzymes involved in proteolysis and/or glycosylation. The reduced capacity of the cells of the invention to proteolytically cleave and/or glycosylate a heterologously expressed polypeptide may be due to structural and/or conformational changes, from the production of one or more enzymes having altered biological properties, from the absence of production of said one or more enzymes or from the production of one or more enzymes at low levels.

In one aspect of the present invention genetically modified Pichia strains are provided wherein at least one nucleic acid sequence encoding a functional gene product and/or at least one nucleic acid necessary for expression of at least one gene product in said Pichia strain is genetically modified, wherein said gene product is responsible for proteolysis and/or glycosylation in said genetically modified Pichia strain. The genetically modified Pichia strains of the present invention include, but are not limited to, Pichia wherein at least one nucleic acid sequences encoding at least one of the following a functional gene product or expression of said gene product is genetically modified: PEP4, PRB1, YPS1, YPS2, YMP1, DAP2, GRH1, PRD1, YSP3, PRB3, YMP2, and/or YMP3. Also included in the present invention are genetically modified Pichia strains which produces a reduced amount, none and/or at least one reduced activity of at least one of the following enzymes and/or type of enzyme: aspartyl proteases, serine proteases, secreted aspartyl proteases, secreted serine proteases, yeast methyltrophic proteases, DPP IV like endopeptidases, metalloendopeptidases, Prb1-like serine proteases, Prb1 serine proteases, CPY like carboxypeptidases and/or mannosyltranferases compared with wild type strain. Additionally, genetically modified strains may produce an enzyme selected from: aspartyl proteases, serine proteases, secreted aspartyl proteases, secreted serine proteases, yeast methyltrophic proteases, DPP IV like endopeptidases, metalloendopeptidases, Prb1-like serine proteases, Prb1 serine proteases, CPY like carboxypeptidases and/or mannosyltranferases wherein said enzyme demonstrates at least one reduced activity of said enzyme compared with a wild type strain and/or enzyme.

Genetically modified Pichia strains of the present invention also include Pichia strains wherein at least one of the following nucleic acid sequences encoding a functional gene product or expression of said gene product is genetically modified: OCH1, PMT1, PMT2, and/or PMT4. The genetically modified Pichia of the present invention produce a reduced amount, no, or reduced activity of at least one mannosyltransferase compared with wild type strain. Additionally, genetically modified strains may produce an enzyme associated with glycosylation such as at least one mannosyltransferase that has a reduced activity compared with wild type enzyme.

Genetically modified Pichia strains of the present invention include, but are not limited to genetically modified form of wild type X-33 or SMD1163 Pichia. Genetically modified Pichia strains of the present invention include, but are not limited to genetically modified form of wild type Pichia pastoris, Pichia finlandica, Pichia trehalophila, Pichia koclamae, Pichia membranaefaciens, Pichia methanolica, Pichia minuta (Ogataea minuta, Pichia lindneri), Pichia opuntiae, Pichia thermotolerans, Pichi salictaria, Pichia guercum, Pichia pijperi, Pichia stiptis, Pichia sp.

In another aspect of the present invention, modified Pichia strains are provided wherein the following nucleic acid sequence encoding a functional gene product or expression of said gene product are genetically modified: PEP4, PRB1, YPS1, YPS2, YMP1, YMP2, YMP3 and PMT4. The modified Pichia of the present invention produce a reduced amount, none or reduced activity of at least one of the following gene products compared with a wild type strain: aspartyl protease, serine protease, serine secreted protease and mannosyltransferase. The modified Pichia strains of the present invention, also have reduced activity of at least one of the following gene products compared with wild type strain: at least one aspartyl protease, at least one serine protease, at least one serine secreted protease and/or at least one mannosyltransferase.

The genetically modified Pichia strains of the present invention may further comprise a polynucleotide capable of expressing at least one heterologous polypeptide. Polynucleotide capable of expressing at least one heterologous polypeptide include, but are not limited to, vectors, DNA transformed into the genome of the host cell, virus or part of a virus, and/or plasmids. Polynucleotide capable of expressing a heterologous polypeptide may be transformed into the genome of the Pichia and/or may be part of an expression vector and/or episomal expression system.

As is understood in the art, DNA may be transformed into a host cell by several different methods. In yeast, any convenient method of DNA transfer may be used, such as electroporation, the lithium chloride method, or the spheroplast method. To produce a stable strain suitable for high-density fermentation, it is desirable to integrate the DNA into the host chromosome. Integration occurs via homologous recombination, using techniques known in the art. For example, DNA capable of expressing at least one heterologous protein can be provided with flanking sequences homologous to sequences of the host organism. In this manner, integration occurs at a defined site in the host genome, without disruption of desirable or essential genes. Alternatively, DNA capable of expressing at least one heterologous protein is integrated into the site of an undesired gene in a host chromosome, effecting the disruption or deletion of the gene or expression of that gene product. For example, integration into the sites of the YMP1, YMP2, YMP3, PEP4, PRB1, YPS1, YPS2, DAP2, GRH1, PRD1, YSP3, PRB3, SEQ ID NO:10, SEQ ID NO:12 and/or SEQ ID NO:14 genes allows the expression of the heterologous protein while preventing the expression of enzymes involved in yeast proteolysis. In other embodiments, DNA may be introduced into the host via a chromosome, plasmid, retroviral vector, or random integration into the host genome.

In another aspect of the present invention, at least one heterologous polypeptide expressed in the host cells of the present invention comprises at least one GLP-1 agonist. In some aspects, the GLP-1 agonist is selected from the group of: incretin hormone and/or fragment, variant and/or conjugate thereof and incretin mimetic and/or fragment, variant and/or conjugate thereof. In some aspects, at least one heterologous polypeptide has at least one GLP-1 activity.

Polypeptides having GLP-1 activity may comprise at least one fragment and/or variant of human GLP-1. The two naturally occurring fragments of human GLP-1 are represented in SEQ ID NO:2.

```
                                                 (SEQ ID NO: 2)
 7   8   9   10  11  12  13  14  15  16  17
His-Ala-Glu-Gly-Thr-Phe-Thr-Ser-Asp-Val-Ser- 18  19  20  21  22  23  24  25  26  27  28
Ser-Tyr-Leu-Glu-Gly-Gln-Ala-Ala-Lys-Glu-Phe- 29  30  31  32  33  34  35  36  37
Ile-Ala-Trp-Leu-Val-Lys-Gly-Arg-Xaa
``` wherein: Xaa at position 37 is Gly (hereinafter designated as "GLP-1(7-37)"), or NH$_2$ (hereinafter designated as "GLP-1(7-36)"). GLP-1 fragments may include, but are not limited to, molecules of GLP-1 comprising, or alternatively consisting of, amino acids 7 to 36 of human GLP-1 (GLP-1(7-36)). Variants of GLP-1 or fragments thereof may include, but are not limited to, one, two, three, four, five or more amino acid substitutions in wild type GLP-1 or in the naturally occurring fragments of GLP-1 shown in SEQ ID NO:2. Variants GLP-1 or fragments of GLP-1 may include, but are not limited to, substitutions of an alanine residue analogous to alanine 8 of wild type GLP-1, such alanine being mutated to a glycine (hereinafter designated as "A8G") (See for example, the mutants disclosed in U.S. Pat. No. 5,545,618, herein incorporated by reference in its entirety).

In another aspect, the at least one polypeptide having GLP-1 activity comprises at least one fragment and/or variant of human GLP-1 fused with human serum albumin. In another aspect, at least one fragment and variant of GLP-1 comprises GLP-1(7-36(A8G)). The at least one fragment and variant of GLP-1 is genetically fused to human serum albumin. In another aspect, the heterologous polypeptide of the present invention comprises at least two GLP-1(7-36(A8G)) tandemly and genetically fused to the human serum albumin. The two GLP-1(7-36(A8G)) are genetically fused at the N-terminus of the human serum albumin. In some instances, the heterologous polypeptide comprises SEQ ID NO:1.

```
                                                                 (SEQ ID NO: 1)
HGEGTFTSDVSSYLEGQAAKEFIAWLVKGRHGEGTFTSDVSSYLEGQAAKEFIAWLVKGR      60

DAHKSEVAHRFKDLGEENFKALVLIAFAQYLQQCPFEDHVKLVNEVTEFAKTCVADESAE     120

NCDKSLHTL FGDKLCTVATLRETYGEMADCCAKQEPERNECFLQHKDDNPNLPRLVRPE     180

VDVMCTAFHDNEETFLKKYLYEIARRHPYFYAPELLFFAKRYKAAFTECCQAADKAACLL     240

PKLDELRDEGKASSAKQRLKCASLQKFGERAFKAWAVARLSQRFPKAEFAEVSKLVTDLT     300

KVHTECCHGDLLECADDRADLAKYICENQDSISSKLKECCEKPLLEKSHCIAEVENDEMP     360

ADLPSLAADFVESKDVCKNYAEAKDVFLGMFLYEYARRHPDYSVVLLLRLAKTYETTLEK     420

CCAAADPHECYAKVFDEFKPLVEEPQNLIKQNCELFEQLGEYKFQNALLVRYTKKVPQVS     480

TPTLVEVSRNLGKVGSKCCKHPEAKRMPCAEDYLSVVLNQLCVLHEKTPVSDRVTKCCTE     540

SLVNRRPCFSALEVDETYVPKEFNAETFTFHADICTLSEKERQIKKQTALVELVKHKPKA     600

TKEQLKAVMDDFAAFVEKCCKADDKETCFAEEGKKLVAASQAALGL                   674
```

In yet another embodiment, at least one heterologous polypeptide expressed in the host cells of the invention comprises one or more of the following: at least one antigen binding protein, at least one single variable domain, and/or at least one domain antibody. Polypeptides comprising at least one antigen binding domain may also comprise at least one polypeptide and/or peptide receptor agonist and/or antagonist. In some instances, the polypeptide agonist may be a GLP-1 receptor agonist. As is understood in the art, more than one heterologous polypeptide may be expressed in the same cell. By way of example, a heterologous polypeptide having GLP-1 activity can be expressed in the same cell as an antigen binding protein. The polypeptide having GLP-1 activity may be expressed from the same polynucleotide as the antigen binding protein, operably linked to the nucleic acid sequenced necessary for expression. Alternatively, and by way of example, a polypeptide having GLP-1 activity may be expressed independently of a second heterologous polypeptide such as an antigen binding protein, either from the same episome DNA or genome but operably linked to different polynucleotide sequences necessary for expression or from DNA sequences located on separate vectors.

Also, provided herein are genetically modified *Pichia* strains, wherein said strain shows reduced proteolysis of said at least one heterologous polypeptide in said strain compared with wild type *Pichia*. In addition, genetically modified *Pichia* of the present invention show reduced or no glycosylation of said at least one heterologous polypeptide in said strain compared with wild type *Pichia*.

In another aspect, methods are provided of producing a heterologous polypeptide comprising expressing said heterologous polypeptide in a genetically modified *Pichia* of the invention. Also provided are heterologous polypeptide produced in anyone of the genetically modified *Pichia* of the present invention.

In yet another aspect of the present invention, isolated polynucleotides having at least 50%, 55%, 60%, 65%, 70%, 75%, 80%, 85%, 90%, 95%, 99%, and/or 100% sequence identity to SEQ ID NO:3, 5, and 7 are provided. In yet another aspect of the present invention, isolated polypeptides having at least 50%, 55%, 60%, 65%, 70%, 75%, 80%, 85%, 90%, 95%, 99%, and/or 100% sequence identity to SEQ ID NO:4, 6, and 8 are provided. Further embodiments include, genetically modified host cells wherein wild type parent of said genetically modified host cell comprises a gene encoding a polypeptide having at least 50%, 55%, 60%, 65%, 70%, 75%, 80%, 85%, 90%, 95%, 99%, and/or 100% sequence identity to SEQ ID NO:4, 6, 8 wherein said gene is genetically modified in the genome of said host cell such that the gene product is reduced or eliminated in said genetically modified host cell compared with said wild type host cell. Also provided are genetically modified host cells wherein said wild type parent of said genetically modified host cell comprises a gene having at least 50%, 55%, 60%, 65%, 70%, 75%, 80%, 85%, 90%, 95%, 99%, and/or 100% sequence identity to SEQ ID NO:3, 5, and 7 wherein said gene is genetically modified in the genome of said genetically modified host cell. The genetically modified host cell of the present invention have reduced or eliminated protease activity compared with said wild type parent host cell. The genetically modified host cell of the present invention have reduced or eliminated yeast methylotropic protease (Ymp1) activity. In some instances, the host cell is *Pichia*.

In yet another aspect of the present invention, isolated polynucleotides having at least 50%, 55%, 60%, 65%, 70%, 75%, 80%, 85%, 90%, 95%, 99%, and/or 100% sequence identity to SEQ ID NO:9, 11 and 13 are provided. In yet another aspect of the present invention, isolated polypeptides having at least 50%, 55%, 60%, 65%, 70%, 75%, 80%, 85%, 90%, 95%, 99%, and/or 100% sequence identity to SEQ ID NO:10, 12 and 14 are provided.

As is understood in the art, the enzymatic activity of one or more enzymes produced by host cells in culture can be affected by the growth conditions of the culture. For example, the proteolytic activity of a protease produced by a host cell in culture could be decreased by altering one or more of the following conditions: pH, dissolved oxygen, temperature, osmolarity, one or more media components, specific protease inhibitors, growth time and/or rate, cell concentration, duration of culture, and/or glucose feed rate (e.g., fed batch). Addition of complex protein hydrolysates to the culture may be especially effective at inhibition of proteolysis. Moreover, the conditions may be altered at one or more specific times during the culture in such a way as to maximize the effect. Similarly, glycosylation of proteins produced in culture can be affected by similar factors. Therefore, growth conditions for reducing enzymatic activity of a host cell, such as proteolytic or glycosylation activity, in culture can be optimized by adjusting one or more of the non-limiting factors listed above.

Also, as is understood in the art production of heterologous protein in a host cell may be increased by controlling many of the same factors noted above. In addition, the addition of factors that increase vector copy number, including, but not limited to, the addition of rapamycin to growth media, may also increase production. Other factors that may increase production include, but are not limited to, co-expression of one or more chaperon proteins, such as protein disulphide isomerase (PDI). Additionally, hemoglobin (HB) can be co-expressed with at least one heterologous polypeptide in a host cell to enhance oxygen availability for oxidative metabolism, thus, increasing polypeptide production.

Heterologous proteins that are secreted from a host cell during production may comprise a leader sequence which facilitates secretion. Leader sequences may be modified to improve secretion and therefore overall production and recovery of heterolgously expressed protein; for example different leader sequences from various secreted proteins may be operably linked to the heterologous protein and assessed for enhanced expression. Alternatively, a given leader sequence may be modified by site directed mutagenesis, or by means of a combinatorial library approach to identify an improved leader sequence variant. Chimeric leader sequences, comprising regions from two or more leader peptides, may be found to improve heterologous protein expression level.

EXAMPLES

The following examples illustrate various non-limiting aspects of this invention.

Example 1—Ymp1 Novel Proteases

A novel protease was identified from *Pichia* culture supernatant using affinity purification and LC/MS analysis. FIG. 1 shows a novel *Pichia* yeast methylotropic protease (Ymp1) identified on the gel. Clarified filtered supernatant from B378 (*Pichia* null strain) was incubated overnight with biotinylated aprotinin. The supernatant was loaded onto a 2 mL avidin column (Pierce) and washed with PBS. The column was eluted sequentially with 0.1M Tris, 2M Sodium chloride, pH7.5, then 0.1M Sodium acetate, 2M Sodium chloride, pH4.5 and finally Biotin Elution Buffer (Pierce). The eluates were concentrated and run on SDS-PAGE. The most prominent bands, Bands 1 and 2 were excised from the gel, reduced, alkylated and digested with trypsin in situ. The tryptic peptides from each band were analyzed by liquid chromatography-tandem mass spectrometry. Un-interpreted sequence data were searched against the *Pichia* contig-peptide database (Integrated Genetics) using Mascot protein identification software.

The peptides generated from both Bands 1 and 2 matched an open reading frame (ORF) in a *Pichia* genome database. The gene was isolated and sequenced, which contains an open reading frame of 5115 bp nucleotide acids (SEQ ID NO:3) encoding a novel protein of 1704 amino acids (SEQ ID NO:4). The predicted molecular weight of the entire protein is 185.8 KD. The polynucleotide sequence of this gene from *Pichia* (shown in SEQ ID NO:3) shares no significant homology with any sequence in GenBank. The encoding amino acid sequence contains two structure domains: the N-terminal domain (AA 1-865) shares 30.2% identities to *Hypocrea lixii* serine endopeptidease, and the C-terminal domain (AA 1305-1449) shares 48% identities to LPXTG-motif cell wall anchor domain protein from *Lactobacillus reuteri*. However, the full-length comparison of SEQ ID NO:4 and *Hypocrea lixii* serine endopeptidase shows only 14.8% identity using William Pearson's LALIGN program calculates a global alignment of two sequences version 2.2u (Myers and Miller, CABIOS (1989) 4:11-17). The predicted structure for this protease is shown in FIG. 2. Its C-terminal structure and sequence are unique among all serine protease of all species. The gene was named as yeast methylotropic protease (YMP1) since it is present in methyltrophic *Pichia* culture. It is a novel class of protease based on its unique structure. Ymp1 is one of the most abundant secreted proteins in *Pichia* methyltrophic culture medium based on a global analysis of *Pichia* culture supernatant using LC/MS (data not shown).

(SEQ ID NO: 3)
```
ATGTTCCTCA AAAGTCTCCT TAGTTTTGCG TCTATCCTAA CGCTTTGCAA GGCCTGGGAT

CTGGAAGATG TACAAGATGC ACCAAAGATC AAAGGTAATG AAGTACCCGG TCGCTATATC

ATTGAGTATG AAGAAGCTTC CACTTCAGCA TTTGCTACCC AACTGAGAGC TGGGGGATAT

GACTTTAACA TCCAATACGA CTACTCAACT GGTTCCCTTT TCAACGGAGC ATCTGTTCAA

ATCAGCAACG ATAACAAAAC CACTTTCCAG GATTTGCAAA GTTTGCGTGC AGTCAAAAAT

GTTTACCCAG CTACTCTCAT TACATTAGAT GAAACATTTG AGCTTGCTGA CACGAAGCCA

TGGAACCCTC ATGGAATTAC CGGTGTCGAT TCTTTGCATG AGCAAGGATA TACTGGTAGT

GGTGTTGTTA TTGCAGTTAT CGATACTGGT GTTGACTATA CACACCCTGC TCTGGGTGGT

GGTATCGGAG ATAATTTCCC TATCAAAGCT GGTTATGATT TGTCTTCCGG TGATGGTGTC

ATCACGAATG ATCCTATGGA TTGTGACGGT CATGGTACCT TTGTATCCTC CATCATTGTT

GCAAATAACA AAGATATGGT TGGTGTTGCA CCAGATGCTC AGATTGTCAT GTACAAAGTG

TTCCCCTGTT CTGATAGTAC TTCGACTGAC ATAGTTATGG CGGGTATGCA AAAGGCCTAT

GATGATGGTC ACAAGATTAT TTCGCTATCA CTGGGATCTG ACTCGGGGTT TTCCAGTACT

CCAGCTTCCT TAATGGCCAG CAGGATTGCT CAAGACAGAG TTGTTTTGGT GGCTGCTGGT

AACTCTGGAG AACTTGGTCC ATTCTATGCC TCCTCCCCTG CTTCTGGGAA ACAAGTCATT

TCAGTTGGAT CTGTTCAAAA CGAACAATGG ACAACCTTTC CAGTAACCTT TACCTCTTCA

AACGGTGAAT CAAGGGTTTT TCCTTACCTC GCTTACAATG GTGCACAGAT TGGATTTGAT

GCCGAGCTTG AGGTTGATTT TACCGAAGAA AGAGGATGCG TCTATGAACC AGAGATCTCC

GCAGATAATG CGAATAAAGC TATTTTGTTA AGAAGGGGCG TCGGCTGTGT TGAAAACTTG

GAATTCAATT TATTGTCTGT GGCTGGTTAC AAGGCTTACT TCTTGTACAA CTCATTTTCA

AGACCATGGA GTCTCTTGAA TATTTCTCCA CTGATTGAGC TAGACAACGC TTACTCTCTT

GTTGAAGAGG AAGTTGGAAT ATGGGTGAAA ACCCAAATCG ACGCCGGTAA CACCGTCAAG

TTAAAGGTGA GCACGAGTGA CCAAATGTTG CCATCTGATA AAGAGTATTT GGGAGTTGGA

AAGATGGATT ATTACTCCTC TCAAGGACCT GCTTATGAGC TTGAATTTTT CCCAACGATA

TCCGCTCCAG GTGGAGACAG TTGGGGCGCT TGGCCCGGTG GGCAATACGG TGTTGCCTCA

GGAACAAGTT TTGCTTGCCC CTATGTTGCA GGTCTTACAG CTCTTTATGA ATCGCAGTTT

GGAATTCAAG ATCCCCAGGA CTATGTGAGA AAATTAGTCT CCACAGCTAC CGATCTTCAA

TTATTTGACT GGAACGCAGT GAAACTTGAG ACCTCTATGA ATGCTCCACT TATTCAACAG

GGAGCTGGTC TAGTGAACGC TCTTGGTTTG TTTGAGACTA AGACTGTGAT CGTGTCTGCT

CCTTATTTGG AGCTCAATGA CACCATCAAT AGAGCCAGTG AGTATACCAT TCAAATTAAG

AATGAGAACT CTGAGACTAT TACCTATCAA GTTGTTCACG TTCCGGGAAC TACTGTCTAC

TCTAGATCAG CTTCTGGGAA CATCCCATAC CTGGTCAATC AAGATTTTGC ACCTTACGGT

GATAGTGATG CTGCGACAGT TGCTCTATCC ACAGAAGAGT TGGTTTTGGG ACCAGGAGAA

GTTGGTGAAG TCACTGTGAT CTTCTCTACA GAAGAAATTG ATCAAGAAAC TGCTCCAATT
```

```
ATTCAGGGTA AGATTACATT TTATGGTGAT GTCATACCGA TTGCTGTTCC TTATATGGGA
GTTGAAGTTG ATATTCATTC CTGGGAGCCT CTCATTGAGA GGCCTTTATC AGTGAGAATG
TATTTGGATG ATGGTTCCTT AGCATATGTT GATGATGATC CTGATTATGA GTTCAATGTG
TATGACTGGG ATTCTCCTAG ATTTTATTTT AACCTGAGAT ATGCAACCAA AGAAGTATCG
ATTGACTTGG TGCACCCTGA TTATAGCATT GAGAACGACT ACGAATGGCC TTTAGTTTCC
GGACACAACA ACTATTATGG TCCCGTGGGA TACGACTACG ATTATACCTC GGGTCAAGCC
TTTTTGCCTC GTTACTTTCA ACAACGTATT AACGAACTTG GATATCTTTC TTTTTCCAGA
TTTGCTAACT TTTCTGTAGT TCCTGCTGGT GAATACAAAG CTCTATTTAG AGTTTTGCTA
CCATATGGAG ACTTTTGGAA CAAAGAAGAC TGGCAATTGT TTGAATCCCC AGTGTTTAAC
GTCCTCGCTC CACCGAATGA AGAAAACACT ACTGAAGAGC CAACTGAGGA ATCCAGCGAG
GAGCCTACCG AAGAGTCAAC GTCTGAGTCA ACTGAAGAGC CCTCTTCTGA GTCAACTGAG
AAATCTAGCG AGGTGCCAAC TGAAGAAATT ACTGAAGATG CAACATCCAC AATTGATGAT
GATGAAGCAT CCACCGAAAG CTCTACTGAA GAACCAAGTG CTCAGCCCAC CGGTCCTTAC
TCTGATTTGA CTGTCGGTGA GGCCATTACC GACGTTAGTG TCACCAGTTT GAGGACAACT
GAAGCATTTG GATACACTTC CGACTGGTTG GTTGTGTCTT TCACTTTCAA CACTACTGAC
AGAGATATTA CTCTCCCACC TTACGCTGTT GTACAAGTAA CTATCCCAAA TGAACTTCAA
TTCATTGCTC ATCCAGAATA CGCCCCATAC CTTGAGCCCT CATTGCAAGT TTTCTACACT
AAGAATGAAA GATTAATTAT GACTAGTCAG TTCAACTACG ACACCAGAGT CATCGACTTC
AAGTTTGACA ATCGAGACCA AGTAATAACT CAAGTGGAGG GAGTTGTTTA TTTCACGATG
AAACTAGAAC AAGATTTCAT TTCTGCATTG GCCCCAGGTG AATACGATTT TGAATTTCAT
ACATCCGTTG ATTCTTATGC TTCGACCTTT GACTTTATTC CATTGATTAG ATCCGAGCCA
ATCAAATTGA TAGCAGGTGC ACCAGACGAA GTTGAATGGT TTATTGATAT TCCAAGTGCA
TACAGCGATT TGGCAACGAT AGATATTAGT TCTGATATCG ATACTAATGA TAATTTGCAG
CAGTACTTCT ATGATTGCTC AAAGCTCAAG TACACTATTG GAAAAGAGTT TGATCAGTGG
GGTAATTTTA CAGCTGGATC AGATGGTAAC CAATACAGCA ATACCACCGA TGGGTATGTT
CCAATTACTG ATTCTACCGG CTCTCCAGTA GCTGAAGTTC AATGTTTAAT GGAAAGTATC
TCATTGAGTT TCACAAATAC TCTTGCTGAG GATGAAGTAT TGAGAGTTGT TCTTCACTCT
TCTGCGTTTA GACGTGGTTC ATTCACCATG GCCAACGTGG TAAACGTTGA CATTACAGCT
GGTGGATTGG CAAAAAGAGA ACTCTTCTCT TATATATTGG ATGAAAATTA CTATGCTAGT
ACTGGATCTG AGGGGTTGGC ATTTGACGTA TTTGAAGTTG CTGATCAGGT CGAGGAGCCA
ACTGAGGAGT CAACCTCAGA GGAATCTACT GAACAGGAAA CTTCCACCGA GGAACCTACC
GAGGAATCAA CTGAACCTAC TGAGGAATCT ACCCAGGAAC CTACTGAAGA GCCCACCGAC
GAGCCTACTT CTGAGTCAAC TGAGGAACCT TCTGAGGAGC CAACTTCTGA CGATCTCTCA
ATTGACCCAA CTGCTGTACC TACCGATGAA CCTACTGAAG AGCCAACTGA GGAGCCTACT
TCTGAGTCAA CTGAGGAACC TTCTGAGGAG CCAACTTCTG ACGATCTCTC AATTGACCCA
ACTGCTGTAC CTACCGATGA ACCTACTGAA GAGCCAACTG AGGAGCCTAC TTCTGAGTCA
ACTGAGGAAC CTTCTGAGGA GCCAACTTCT GACGATCTCT CAATTGACCC AACTGCTGTA
CCTACCGATG AACCTACTGA AGAGCCAACT GAGGAGCCGA CCTCTGAGAC TACCGATGAT
CCATCGATAG CACCTACTGC TGTGCCAACT TCCGACACAT CTTCTGGACA ATCGGTGGTT
ACTCAAAACA CTACAGTCAC TCAGACTACC ATCACTTCAG TCTGTAATGT TTGTGCTGAG
```

```
-continued
ACCCCTGTAA CAATCACTTA CACTGCACCA GTTGTGACTA AGCCAGTTTC TTACACCACC

GTTACTTCAG TTTGCCATGT ATGTGCAGAG ACACCAATCA CAGTTACCTT GACGTTGCCA

TGTGAAACCG AAGACGTGAC AAAGACTGCC GGCCCTAAGA CTGTCACTTA CACCGAAGTT

TGCAACTCCT GTGCTGACAA GCCTATCACT TACACCTACA TCGCTCCAGA GTACACTCAA

GGTGCCGAAC GTACAACAGT TACATCGGTT TGCAACGTTT GTGCTGAGAC ACCTGTAACG

CTAACATACA CTGCGCCGAA AGCCAGTCGT CATACAGTTC CTTCACAATA TTCAAGTGCC

GGAGAGCTCA TTTCATCCAA GGGGATCACG ATTCCTACTG TTCCTGCCCG TCCAACTGGT

ACTTATAGTA AGTCTGTTGA CACTAGCCAA CGTACACTCG CTACCATTAC AAAATCTTCA

GATGAGTCTA ACACTGTTAC CACTACTCAA GCCACACAAG TTTTGAGCGG TGAATCCAGT

GGAATTCAAG CTGCTTCAAA CAGCACGAGC ATCTCAGCTC CAACTGTCAC TACAGCTGGG

AACGAGAACT CTGGATCTAG ATTTTCGTTT GCTGGACTAT TCACAGTTCT GCCTCTTATC

TTGTTCGTTA TATAA
```

The polypeptide sequence encoded by the gene sequence of SEQ ID NO:3 is presented below as SEQ ID NO:4.

```
                                                         (SEQ ID NO: 4)
MFLKSLLSFA SILTLCKAWD LEDVQDAPKI KGNEVPGRYI IEYEEASTSA FATQLRAGGY

DFNIQYDYST GSLFNGASVQ ISNDNKTTFQ DLQSLRAVKN VYPATLITLD ETFELADTKP

WNPHGITGVD SLHEQGYTGS GVVIAVIDTG VDYTHPALGG GIGDNFPIKA GYDLSSGDGV

ITNDPMDCDG HGTFVSSIIV ANNKDMVGVA PDAQIVMYKV FPCSDSTSTD IVMAGMQKAY

DDGHKIISLS LGSDSGFSST PASLMASRIA QDRVVLVAAG NSGELGPFYA SSPASGKQVI

SVGSVQNEQW TTFPVTFTSS NGESRVFPYL AYNGAQIGFD AELEVDFTEE RGCVYEPEIS

ADNANKAILL RRGVGCVENL EFNLLSVAGY KAYFLYNSFS RPWSLLNISP LIELDNAYSL

VEEEVGIWVK TQIDAGNTVK LKVSTSDQML PSDKEYLGVG KMDYYSSQGP AYELEFFPTI

SAPGGDSWGA WPGGQYGVAS GTSFACPYVA GLTALYESQF GIQDPQDYVR KLVSTATDLQ

LFDWNAVKLE TSMNAPLIQQ GAGLVNALGL FETKTVIVSA PYLELNDTIN RASEYTIQIK

NENSETITYQ VVHVPGTTVY SRSASGNIPY LVNQDFAPYG DSDAATVALS TEELVLGPGE

VGEVTVIFST EEIDQETAPI IQGKITFYGD VIPIAVPYMG VEVDIHSWEP LIERPLSVRM

YLDDGSLAYV DDDPDYEFNV YDWDSPRFYF NLRYATKEVS IDLVHPDYSI ENDYEWPLVS

GHNNYYGPVG YDYDYTSGQA FLPRYFQQRI NELGYLSFSR FANFSVVPAG EYKALFRVLL

PYGDFWNKED WQLFESPVFN VLAPPNEENT TEEPTEESSE EPTEESTSES TEEPSSESTE

KSSEVPTEEI TEDATSTIDD DEASTESSTE EPSAQPTGPY SDLTVGEAIT DVSVTSLRTT

EAFGYTSDWL VVSFTFNTTD RDITLPPYAV VQVTIPNELQ FIAHPEYAPY LEPSLQVFYT

KNERLIMTSQ FNYDTRVIDF KFDNRDQVIT QVEGVVYFTM KLEQDFISAL APGEYDFEFH

TSVDSYASTF DFIPLIRSEP IFLIAGAPDE VEWFIDIPSA YSDLATIDIS SDIDTNDNLQ

QYFYDCSKLK YTIGKEFDQW GNFTAGSDGN QYSNTTDGYV PITDSTGSPV AEVQCLMESI

SLSFTNTLAE DEVLRVVLHS SAFRRGSFTM ANVVNVDITA GGLAKRELFS YILDENYYAS

TGSEGLAFDV FEVADQVEEP TEESTSEEST EQETSTEEPT EESTEPTEES TQEPTEEPTD

EPTSESTEEP SEEPTSDDLS IDPTAVPTDE PTEEPTEEPT SESTEEPSEE TSDDLSIDPT

AVPTDEPTEE PTEEPTSEST EEPSEEPTSD DLSIDPTAVP TDEPTEEPTE EPTSETTDDP
```

```
                                                    -continued
SIAPTAVPTS DTSSGQSVVT QNTTVTQTTI TSVCNVCAET PVTITYTAPV VTKPVSYTTV

TSVCHVCAET PITVTLTLPC ETEDVTKTAG PKTVTYTEVC NSCADKPITY TYIAPEYTQG

AERTTVTSVC NVCAETPVTL TYTAPKASRH TVPSQYSSAG ELISSKGITI PTVPARPTGT

YSKSVDTSQR TLATITKSSD ESNTVTTTQA TQVLSGESSG IQAASNSTSI SAPTVTTAGN

ENSGSRFSFA GLFTVLPLIL FVI.
```

Example 2—Novel Proteases

Two additional novel yeast methylotropic proteases (Ymp2 and Ymp3) were identified using similar affinity purification and LC/MS analysis as described in Example 1 from supernatant of a *Pichia* ymp1 knockout strain (see Example 3). Clarified filtered supernatant from B580 (*Pichia* ymp1 deletion strain) was incubated overnight with biotinylated AEBSF (4-(2-Aminoethyl) benzenesulfonyl fluoride hydrochloride). The supernatant was loaded onto a 10 mL avidin column (Pierce) and washed with PBS. The column was eluted sequentially with 0.1M Tris, 2M Sodium chloride, pH7.5, then 0.1M Sodium acetate, 2M Sodium chloride, pH4.5 and finally Biotin Elution Buffer (Pierce). The eluates were denatured by adding 8 M urea, and the Cys residues were reduced by reaction with 20 mM dithiothreitol (DTT) and then alkylated by reaction with 20 mM iodoacetamide. After diluting the sample to 2 M urea with 100 mM ammonium bicarbonate (pH 8.5), proteins were digested by trypsin (Sequencing grade modified trypsin, Promega, Madison, Wis.). The resulted peptides mixture from the digestion was desalted with a PepClean spin column (Pierce, Rockford, Ill.), and analyzed by a LC-MS/MS system, in which a high pressure liquid chromatography (HPLC) with a 75 micrometer inner diameter reverse phase C18 column was on-line coupled with an ion trap mass spectrometer (Thermo, Palo Alto, Calif.). The mass spectrometric data acquired from LC-MS/MS analysis were used to search against the recent Non-Redundant Protein Database from GenBank as well as *Pichia* database (Integrated Genetics) using Mascot protein identification software.

Through peptide matches, two genes, named YMP2 and YMP3 were identified to share homologies with known proteases. YMP2 contains an open reading frame of 618 bp nucleotide acids (SEQ ID NO:5) encoding a novel protein of 205 amino acids (SEQ ID NO:6). The predicted molecular weight of the entire protein is 22.9 KD. The polynucleotide sequence of this gene from *Pichia* (shown in SEQ ID NO:5) shares no significant homology with any sequence in GenBank. However, the encoding amino acid sequence shares 29% identities to the Arginine/Alanine aminopeptidase from *Pichia pastoris*.

```
                                                                   (SEQ ID NO: 5)
            ATGGCTCCCA GAACACTACC AGAAGACTTA ATTCCCTCCC TATACGACTT GCACATCTAC

AACTTCCAAC CCGAAAAAAA GACTTATGAT GGAGACATTG TCATCCACTT GGAGGTGAAG

GAGCCCACTG ATGAAGTGGT CTTCAATGCC AAGGATTTGG AATTGAAAGA CGTACATGTC

TTCCACAATG TCAACAAGTC TGAAAACGAA ATCCCCGTTA AGGAGATTGT TGATAACGAG

CTCATCACAA TTAAGCTCAA AGAGAAGGTT ACTTCCGGAA CGTTGCTGGT GAATATTTCC

TTCACCGGTA ACATTCAATC TGATAAAATT GGATTTTACA AGGGAGACAC AGATGTGGAA

GGAAGAGTCA CATACACTAC AAACCTTACC ACTCCAAATG CCAGGTTGGC ATTCCCATGT

CTTGATAACA TATTGTTGAA AGCTCCATTC AAGTTCGGAG TAACTGCCAA TCCAGGACAA

TTAGTGAGTT CCATTTTGGA TCTAAGCTCT GAGGCTGACG TCTTGAATGA CAATGACGAT

GTGATTGGTA CGAGATACCA ATACCAAGTG AGTGAGCCAA TAGCCCCAGC TTTACTGGAG

TGGACCATTC ATATTTAA
```

The polypeptide sequence encoded by the gene sequence of SEQ ID NO:5 is presented below as SEQ ID NO:6.

```
                                                        (SEQ ID NO: 6)
        MAPRTLPEDL IPSLYDLHIY NFQPEKKTYD GDIVIHLEVK EPTDEVVFNA KDLELKDVHV

FHNVNKSENE IPVKEIVDNE LITIKLKEKV TSGTLLVNIS FTGNIQSDKI GFYKGDTDVE

GRVTYTTNLT TPNARLAFPC LDNILLKAPF KFGVTANPGQ LVSSILDLSS EADVLNDNDD

VIGTRYQYQV SEPIAPALLE WTIHI
```

YMP3 contains an open reading frame of 1233 bp nucleotide acids (SEQ ID NO:7) encoding a novel protein of 410 amino acids (SEQ ID NO:8). The predicted molecular weight of the entire protein is 46.0 KD. Its amino acid sequence shares 47% identities to leucine aminopeptidase from *Pichia stipitis*.

```
                                                          (SEQ ID NO: 7)
ATGGTCAAAC TCATATCAAT TATAGCCCTA GTTCAACTTG TCTCTGCGAC AATTGTACCT

TGGAATCTCC AGAACGTCTT ATCTGACGTC CATCACCCTT CTCTCCATCT CTTGGATTAT

ATTCAATCCT TGAAGAACGA GGTAATGTTC GATGGCGACG ATCGCAGAAT AATCAAGTTA

GGCCCCCAAG AATACCGTAT TATCACTGAA AAAGAGAAAT ACCAGTTGAA AACAGAGGGG

ATATCATTTA TCGATGTCAC CTATCAGCAT GGAGACAATG TAGAGCTGCT CTATTCCAGT

GCGCCAGTTA CCGTTCCAGA CTATCTTTAT CCGTCCAATG ATACTTTCCA TTTCAAACAA

GTAAATTCTT TGATAGGTGA GATTGACATT GGCAGAATGC AGGCGTTTTT GGGAAGGTTC

TCTAGCTTCT TTACAAGATT TTACAAATCT GACAAGGGGT TGCAGAGTTC TATCTGGTTA

CAAGGTGAAT TGGTTCAATT GGCCTTGAAA GATCCATCGA GGTTCAATGT TACTACTGTG

GAACACCCTT GGAAGCAGAA TTCTGCCATC TTTACGATAT ACGGTGAAAA TGTTGATCCT

TCGAAAGGAA AAGGGGACAT TGTAGTAGTG GGATGCCATC AAGATTCCAT AAACTTGCTT

TTCCCCAACA TTCTCCGTGC TCCAGGGGCT GATGATGATG GATCTGGTGT AACTTCCAAC

CTTGAAGCGC TCAGAATCAT AGTTGAAAGT GGCCTCAAGT TTCACAATAC AGTAGAGTTT

CACTTTTATT CTGCCGAAGA AGGAGGACTA CTTGGCTCCC AGCAAATTTT CAGCTCGTAT

AGAGCTGCAG AAGAGACTGT TGTTGCTATG CTACAACAGG ACATGACTGG ATACATCCAA

AAAGCTTTAG ACCACGGGGA ATCCGACCAC TTCGGGCTAA TCACTGACCA TACAAACGCA

AATCTGAATA GCTTCCTTGC ACTTTTAATC GATGCATACA CTTCAATTCC CTACAAAGAA

ACCGAATGTG GGTATGCCTG CTCAGATCAT AGTTCTGCCT TGGAACATGG TTATCCATCT

GCCATGGTCT TTGAAAGTAG TTTTGCCTAC ACAAATCCCT TCATCCATAG CACCCAAGAC

ACAATTGACA AGATCAATTT TCCACATATG GCAGAGCAT GTCAAGTTGG TCCTGGGTTA

CGTTGTAGAG TTGGGATTAG AACATTTTAG GTGA
```

The polypeptide sequence encoded by the gene sequence of SEQ ID NO:7 is presented below as SEQ ID NO:8.

```
                                                          (SEQ ID NO: 8)
MVKLISIIAL VQLVSATIVP WNLQNVLSDV HHPSLHLLDY IQSLKNEVMF DGDDRRIIKL

GPQEYRIITE KEKYQLKTEG ISFIDVTYQH GDNVELLYSS APVTVPDYLY PSNDTFHFKQ

VNSLIGEIDI GRMQAFLGRF SSFFTRFYKS DKGLQSSIWL QGELVQLALK DPSRFNVTTV

EHPWKQNSAI FTIYGENVDP SKGKGDIVVV GCHQDSINLL FPNILRAPGA DDDGSGVTSN

LEALRIIVES GLKFHNTVEF HFYSAEEGGL LGSQQIFSSY RAAEETVVAM LQQDMTGYIQ

KALDHGESDH FGLITDHTNA NLNSFLALLI DAYTSIPYKE TECGYACSDH SSALEHGYPS

AMVFESSFAY TNPFIHSTQD TIDKINFPHM AEHVKLVLGY VVELGLEHFR
```

Additionally, three other potential proteases were identified using all known yeast proteases against *Pichia* database. The identified polynucleotide sequences encoding these proteases and their respective polypeptide sequences are presented in SEQ ID NOs: 9-14 below.

```
                                                          (SEQ ID: 9)
ATGAAATCGG TTATTTGGAG CCTTCTATCT TTGCTAGCAT TGTCGCAGGC ATTGACTATT

CCATTGCTGG AAGAGCTTCA ACAGCAAACA TTTTTTAGCA AGAAAACCGT TCCTCAACAA

GTTGCTGAAT TGGTGGGCAC CCATTACTCT AAGGATGAGA TAATCAGTCT ATGGAAGGAC

ATTGAGCTGG ATGTACCCAG GGAAAAGATC CAAGAGGCCT TCGATAAGTT CGTAAAACAA
```

-continued

```
TCAACTGCCA CTTCCCCCGT TAGAAATGAA TTTCCCTTGT CTCAGCAAGA TTGGGTGACA
GTGACCAACA CCAAGTTTGA TAATTATCAA TTGAGGGTTA AAAAATCCCA CCCTGAAAAG
CTAAACATTG ATAAGGTAAA GCAATCTTCG GGATACCTGG ATATCATTGA TCAAGATAAG
CATCTTTTCT ATTGGTTTTT TGAATCCCGA AATGATCCGT CCACAGACCC AATCATCCTA
TGGTTGAATG GTGGACCCGG CTGCTCTTCT ATTACAGGGT TGCTATTCGA AAAGATTGGC
CCCAGTTACA TCACCAAAGA GATTAAGCCG AACATAATC CTTATTCATG AACAACAAT
GCTAGTGTTA TCTTCCTTGA GCAACCGGTT GGAGTAGGAT TTTCTTACTC TTCTAAGAAA
GTCGGTGATA CTGCAACTGC TGCCAAAGAT ACATATGTGT TTTTGGAGCT TTTCTTCCAA
AAGTTTCCTC AGTTCCTGAC CTCTAATCTG CACATTGCTG GGGAATCGTA TGCTGGCCAT
TATTTGCCCA AGATTGCTTC TGAGATTGTG TCTCACGCAG ACAAGACGTT TGACCTTTCA
GGAGTCATGA TCGGTAATGG TCTTACTGAT CCTCTAATTC AGTATAAGTA CTATCAGCCA
ATGGCCTGTG GAAAAGGTGG CTACAAGCAG GTCATTTCGG ACGAGGAATG TGATGAATTG
GATAGGGTCT ATCCAAGATG TGAACGTTTA ACGCGGGCAT GTTATGAGTT CCAAAATTCA
GTTACTTGTG TTCCGGCAAC ACTTTATTGC GACCAAAAGC TACTGAAGCC GTACACTGAC
ACTGGCTTGA ATGTCTATGA TATTCGTACA ATGTGCGATG AAGGGACTGA TTTGTGTTAC
AAAGAACTGG AATACGTGGA GAAGTACATG AACCAGCCTG AAGTGCAGGA AGCCGTGGGC
TCTGAAGTCA GTTCTTACAA AGGTTGTGAC GATGATGTCT TCTTAAGATT TTTGTACTCT
GGCGATGGAT CTAAGCCTTT CCACCAGTAT ATCACGGATG TTCTCAATGC AAGTATTCCG
GTTCTGATTT ACGCAGGTGA TAAAGATTAT ATCTGTAATT GGCTAGGAAA CCAAGCTTGG
GTCAATGAGC TAGAATGGAA CTTGTCTGAG GAATTCCAGG CAACTCCGAT TCGACCGTGG
TTCACTTTGG ACAATAACGA TTATGCAGGA AACGTACAAA CTTATGGAAA CTTTTCCTTT
CTAAGAGTAT TTGATGCTGG TCACATGGTT CCTTACAATC AACCAGTCAA CGCACTTGAC
ATGGTTGTCA GATGGACACA CGGTGATTTC TCATTTGGTT ATTAA
                                                          (SEQ ID No: 10)
MKSVIWSLLS LLALSQALTI PLLEELQQQT FFSKKTVPQQ VAELVGTHYS KDEIISLWKD
IELDVPREKI QEAFDKFVKQ STATSPVRNE FPLSQQDWVT VTNTKFDNYQ LRVKKSHPEK
LNIDKVQSS GYLDIIDQDK HLFYWFFESR NDPSTDPIIL WLNGGPGCSS ITGLLFEKIG
PSYITKEIKP EHNPYSWNNN ASVIFLEQPV GVGFSYSSKK VGDTATAAKD TYVFLELFFQ
KFPQFLTSNL HIAGESYAGH YLPKIASEIV SHADKTFDLS GVMIGNGLTD PLIQYKYYQP
MACGKGGYKQ VISDEECDEL DRVYPRCERL TRACYEFQNS VTCVPATLYC DQKLLKPYTD
TGLNVYDIRT MCDEGTDLCY KELEYVEKYM NQPEVQEAVG SEVSSYKGCD DDVFLRFLYS
GDGSKPFHQY ITDVLNASIP VLIYAGDKDY ICNWLGNQAW VNELEWNLSE EFQATPIRPW
FTLDNNDYAG NVQTYGNFSF LRVFDAGHMV PYNQPVNALD MVVRWTHGDF SFGY
                                                          (SEQ ID No: 11)
ATGATATTAC ACACCTATAT TATTCTCTCG TTATTGACTA TATTTCCTAA AGCTATTGGT
CTGTCCTTGC AGATGCCAAT GGCCTTGGAA GCTAGTTATG CCTCATTAGT GGAGAAAGCA
ACCCTCGCTG TTGACAAGA AATTGATGCC ATACAAAAGG GTATTCAGCA AGGTTGGTTG
GAAGTAGAGA CAAGATTTCC AACTATAGTG TCACAGTTAT CCTATAGTAC TGGCCCAAAA
TTTGCGATCA AGAAGAAAGA TGCAACTTTT TGGGATTTCT ATGTTGAAAG TCAAGAGTTG
CCAAACTACC GAATTAATGA AAATCTGAAA CCAATTTTCA ACCCCTATTC GTGGAATGGT
AATGCTTCAA TCATCTACTT AGATCAACCG GTCAATGTTG GGTTTTCTTA TTCTTCATCA
```

-continued
```
TCGGTGAGTA ACACTGTTGT TGCGGGAGAA GATGTGTATG CATTTCTTCA GCTTTTTTTT

CAACACTTCC CGGAATATCA AACTAATGAC TTTCATATTG CCGGTGAATC TTATGCAGGA

CATTACATTC CGGTGTTTGC AGACGAAATT TTGAGTCAAA GAACAGAAA TTTCAATCTT

ACTTCAGTCT TGATCGGAAA TGGATTAACT GACCCTTTGA CTCAATACCG ATATTACGAG

CCAATGGCTT GTGGTGAAGG TGGTGCCCCG TCAGTACTGC CTGCCGATGA GTGCGAAAAT

ATGCTAGTTA CCCAAGATAA ATGTTTGTCT TTAATTCAAG CATGCTACGA CTCACAGTCG

GCATTCACAT GCGCACCGGC TGCCATTTAT TGTAATAACG CTCAGATGGG ACCCTATCAG

AGAACTGGGA AGAATGTGTA TGATATTCGT AAGGAATGTG ATGGTGGATC CTTGTGCTAT

AAGGACCTTG AATTCATCGA TACCTACTTA AATCAAAAGT TTGTTCAAGA TGCTTTGGGC

GCCGAGGTCG ATACCTATGA ATCTTGCAAT TTTGAAATCA ACAGAAACTT TTTATTTGCT

GGAGATTGGA TGAAACCTTA TCATGAACAT GTCAGCAGTC TCTTGAACAA AGGTTTGCCC

GTTTTGATTT ACGCAGGGGA CAAAGATTTC ATTTGCAACT GGTTGGGTAA TCGAGCATGG

ACTGATGTCT TGCCGTGGGT TGATGCTGAT GGTTTTGAAA AGCCGAAGT CCAAGATTGG

TTGGTTAATG GAAGGAAGGC TGGTGAATTT AAGAACTATA GCAACTTCAC CTACCTAAGG

GTTTATGATG CTGGTCATAT GGCCCCATAT GATCAGCCAG AGAATTCTCA TGAAATGGTC

AATAGATGGA TATCCGGAGA CTTTAGCTTT CACTAG
```
(SEQ ID No: 12)
```
MILHTYIILS LLTIFPKAIG LSLQMPMALE ASYASLVEKA TLAVGQEIDA IQKGIQQGWL

EVETRFPTIV SQLSYSTGPK FAIKKKDATF WDFYVESQEL PNYRINENLK PIFNPYSWNG

NASIIYLDQP VNVGFSYSSS SVSNTVVAGE DVYAFLQLFF QHFPEYQTND FHIAGESYAG

HYIPVFADEI LSQKNRNFNL TSVLIGNGLT DPLTQYRYYE PMACGEGGAP SVLPADECEN

MLVTQDKCLS LIQACYDSQS AFTCAPAAIY CNNAQMGPYQ RTGKNVYDIR KECDGGSLCY

KDLEFIDTYL NQKFVQDALG AEVDTYESCN FEINRNFLFA GDWMKPYHEH VSSLLNKGLP

VLIYAGDKDF ICNWLGNRAW TDVLPWVDAD GFEKAEVQDW LVNGRKAGEF KNYSNFTYLR

VYDAGHMAPY DQPENSHEMV NRWISGDFSF H
```
(SEQ ID No: 13)
```
ATGCAATTGC GTCATTCCGT TGGATTGGCT ATCTTATCTG CCATAGCAGT CCAAGGATTG

CTAATTCCTA ACATTGAGTC ATTACCCAGC CAGTTTGGTG CTAATGGTGA CAGTGAACAA

GGTGTATTAG CCCACCATGG TAAACATCCT AAAGTTGATA TGGCTCACCA TGGAAAGCAT

CCTAAAATCG CTAAGGATTC CAAGGGACAC CCTAAGCTTT GCCCTGAAGC TTTGAAGAAG

ATGAAGAAG GCCACCCTTC GGCTCCAGTC ATTACTACCC ATTCCGCTTC TAAAAACTTA

ATCCCTTACT CTTATATTAT AGTCTTCAAG AAGGGTGTCA CTTCAGAGGA TATCGACTTC

CACCGTGACC TTATCTCCAC TCTTCATGAA GAGTCTGTGA GCAAATTAAG AGAGTCAGAT

CCAAATCACT CATTTTTCGT TTCTAATGAG AATGGCGAAA CAGGTTACAC CGGTGACTTC

TCCGTTGGTG ACTTGCTCAA GGGTTACACC GGATACTTCA CGGATGACAC TTTAGAGCTT

ATCAGTAAGC ATCCAGCAGT TGCTTTCATT GAAAGGGATT CGAGAGTATT TGCCACCGAT

TTTGAAACTC AAAACGGTGC TCCTTGGGGT TTGGCCAGAG TCTCTCACAG AAAGCCTCTT

TCCCTAGGCA GCTTCAACAA GTACTTATAT GATGGAGCTG GTGGTGAAGG TGTTACTTCC

TATGTTATCG ATACAGGTAT CCACGTCACT CACAAAGAAT TCCAGGGTAG AGCATCTTGG

GGTAAGACCA TTCCAGCTGG AGACGTTGAT GACGATGGAA ACGGTCACGG AACTCACTGT

GCTGGTACCA TTGCTTCTGA AAGCTACGGT GTTGCCAAGA AGGCTAATGT TGTTGCCATC

AAGGTCTTGA GATCTAATGG TTCTGGTTCG ATGTCAGATG TTCTGAAGGG TGTTGAGTAT
```

```
                                                                (SEQ ID No: 14)
GCCACCCAAT CCCACTTGGA TGCTGTTAAA AAGGGCAACA AGAAATTTAA GGGCTCTACC

GCTAACATGT CACTGGGTGG TGGTAAATCT CCTGCTTTGG ACCTTGCAGT CAATGCTGCT

GTTAAGAATG GTATTCACTT TGCCGTTGCA GCAGGTAACG AAAACCAAGA TGCTTGTAAC

ACCTCGCCAG CAGCTGCTGA GAATGCCATC ACCGTCGGTG CATCAACCTT ATCAGACGCT

AGAGCTTACT TTTCTAACTA CGGTAAATGT GTTGACATTT TCGCTCCAGG TTTAAACATT

CTTTCTACCT ACACTGGTTC GGATGACGCA ACTGCTACCT TGTCTGGTAC TTCAATGGCC

TCTCCTCACA TTGCTGGTCT GTTGACTTAC TTCCTATCAT TGCAGCCTGC TGCTGGATCT

CTGTACTCTA ACGGAGGATC TGAGGGTGTC ACACCTGCTC AATTGAAAAA GAACCTCCTC

AAGTATGCAT CTGTCGGAGT ATTAGAGGAT GTTCCAGAAG ACACTCCAAA CCTCTTGGTT

TACAATGGTG GTGGACAAAA CCTTTCTTCT TTCTGGGGAA AGGAGACAGA AGACAATGTT

GCTTCCTCCG ACGATACTGG TGAGTTTCAC TCTTTTGTGA ACAAGCTTGA ATCAGCTGTT

GAAAACTTGG CCCAAGAGTT TGCACATTCA GTGAAGGAGC TGGCTTCTGA ACTTATTTAG (SEQ ID No: 14)
MQLRHSVGLA ILSAIAVQGL LIPNIESLPS QFGANGDSEQ GVLAHHGKHP KVDMAHHGKH

PKIAKDSKGH PKLCPEALKK MKEGHPSAPV ITTHSASKNL IPYSYIIVFK KGVTSEDIDF

HRDLISTLHE ESVSKLRESD PNHSFFVSNE NGETGYTGDF SVGDLLKGYT GYFTDDTLEL

ISKHPAVAFI ERDSRVFATD FETQNGAPWG LARVSHRKPL SLGSFNKYLY DGAGGEGVTS

YVIDTGIHVT HKEFQGRASW GFTIPAGDVD DDGNGHGTHC AGTIASESYG VAKKANVVAI

KVLRSNGSGS MSDVLKGVEY ATQSHLDAVK KGNKKFKGST ANMSLGGGKS PALDLAVNAA

VKNGIHFAVA AGNENQDACN TSPAAAENAI TVGASTLSDA RAYFSNYGKC VDIFAPGLNI

LSTYTGSDDA TATLSGTSMA SPHIAGLLTY FLSLQPAAGS LYSNGGSEGV TPAQLKKNLL

KYASVGVLED VPEDTPNLLV YNGGGQNLSS FWGKETEDNV ASSDDTGEFH SFVNKLESAV

ENLAQEFAHS VKELASELI
```

Example 3—Protease Knockouts

Several *Pichia* knockout strains were generated by the following methods. The 5' end the gene to be knocked out (200-500 bp) was amplified from *Pichia* genomic DNA by PCR using a 5' gene specific primer and a 3' gene specific primer with a 20 bp sequence complementary to the 5' end of selection marker expression cassette, e.g. KanMX. The 3' end the gene to be knocked out (200-500 bp) was also amplified from *Pichia* genomic DNA by PCR using a 5' gene specific primer with a 20 bp sequence complementary to the 3' end of KanMX expression cassette and a 3' gene specific primer. In a separate PCR reaction, a proper amount of 5' product, 3' product, DNA containing KanMX expression cassette, and the 5' and 3' gene specific primers used before were added to make a knockout cassette which has the KanMX expression cassette flanking 5' and 3' homologous regions of the knockout gene. The DNA fragment was purified and transformed into *Pichia* using a standard electroporation method. The recombinant cells were selected on the YPD plates containing an antibiotic, e.g. KAN, and screened by PCR using specific primers. The resulting knockout strains were confirmed by genomic sequencing and Southern blot analysis.

Single and multiple knockouts were then transformed with DNA capable of expressing a heterologous polypeptide. Each knockout strain was transformed with at least one vector encoding the therapeutic protein described by SEQ ID NO:1. Cultures of transformed knockouts were grown and supernatants were harvested. Secreted products were run on NuPAGE MOPS gels for detection of product breakdown by proteolysis. Multiple bands of semi-purified heterologous protein were interpreted to indicate protease activity while a single band of heterologous protein at the appropriate molecular weight was interpreted as no protease activity. See FIG. 5-8.

Protease activity in fermentation supernatant samples was measured using a synthetic peptide with a fluorescent label and quencher with excitation and emission wavelengths of 340 and 405 nm respectively. The peptide substrate was incubated with culture supernatant samples and the rate of degradation of the substrate was monitored using fluorescent HPLC. Results are expressed as increase in peak area/hr. In FIG. 3, protease activity in the fermentation supernatant was around 68-285 in ymp1 mutant strain, while the protease activity in the control strain was around 1541-1909. Accordingly, the mutant strain demonstrated a dramatic reduction of protease activity on the peptide.

Zymogram gel is another method to measure protease activity using casein or gelatin as substrates. In this experiment, fermentation samples were separated on acrylamide gels with either casein or gelatin incorporated into the matrix under reducing, non-denatured conditions. Following separation, the protein bands were renatured and a developing buffer was applied to provide the necessary cofactors for protease activity. The gel was incubated at 37° C. for an extended period and then stained with coomassie blue. Areas of proteolytic activity were identified as clear areas on the gel against a blue background. The active proteases degraded the substrate not allowing the area on the gel to bind the coomassie blue. Areas on the gel lacking active protease allowed the stain to bind to the substrate, thus generating the blue background. FIG. 4 showed the protease active areas using fermentation supernatants from ymp1 mutant strains and two control strains. The control strains had active proteases that migrated both at high and low molecular weight areas. However, the signals at the high molecular weight area were greatly diminished or missing in ymp1 mutant strains. These data show that the activities at the high molecular weight areas could be due to the action of ymp1. Summary results for knockouts are presented in Table 5.

Further studies using buffer stability assay demonstrated the cleavage efficiency and site changes when YMP1 and YPS1 were deleted from the *Pichia* host strains. In this assay, the protein standard described by SEQ ID NO:1 was incubated with the culture supernatants and the cleaved protein products were analyzed by mass spectrophotometry to indicate the cleavage sites and percentage of cleavage products (Table 1-4).

Using the supernatant of the fermentation broth B804 (parental strain SMD1163 with pmt4 deletion, see Example 4), 5 major cleavage sites were detected: Lys28/Gly29, Phe36/Thr37, Ser38/Asp39, Tyr43/Leu44 and Lys50/Glu51 (Table 1).

TABLE 1

Fermentation broth B804 of SMD1163_pmt4 (1:40)

| Sequence | 0 hr | 24 hr | 48 hr | 5 day |
| --- | --- | --- | --- | --- |
| His1-Leu645 | 100 | 73.4 | 33.9 | 4.6 |
| (Trp)Leu26-Leu645 | 0 | 1.4 | 1.8 | 0 |
| (Leu)Val27-Leu645 | 0 | 0 | 0 | 0 |
| (Lys)Gly29-Leu645 | 0 | 5.9 | 6.3 | 1.9 |
| (Phe)Thr37-Leu645 | 0 | 8.7 | 28.4 | 31.7 |
| (Thr)Ser38-Leu645 | 0 | 1 | 0 | 0 |
| (Ser)Asp39-Leu645 | 0 | 4.6 | 12.9 | 18 |
| (Val)Ser41-Leu645 | 0 | 0 | 0 | 0 |
| (Ser)Ser42-Leu645 | 0 | 0 | 2.3 | 2.2 |
| (Tyr)Leu44-Leu645 | 0 | 1.9 | 5.8 | 5.3 |
| (Lys)Glu51-Leu645 | 0 | 4.1 | 8.8 | 28 |
| (Ala)Trp55-Leu645 | 0 | 0 | 0 | 3.4 |
| (Trp)Leu56-Leu645 | 0 | 0 | 0 | 4.9 |

Deletion of the YMP1 from SMD1163_pmp4 (B688) diminished the cleavage sites of Phe36/Thr37, Ser38/Asp39 and Tyr43/Leu44, but maintained or increased the cleavage at Lys50/Glu51 and Lys28/Gly29 (Table 2).

TABLE 2

Fermentation broth B688 of ymp1 KO strain of SMD1163_pmt4 (1:40)

| Sequence | 0 hr | 24 hr | 48 hr |
| --- | --- | --- | --- |
| His1-Leu645 | 93.1 | 75.1 | 64.9 |
| (Trp)Leu26-Leu645 | 0 | 0 | 0 |
| (Leu)Val27-Leu645 | 0 | 0 | 0 |
| (Lys)Gly29-Leu645 | 1.4 | 18.5 | 26 |
| (Phe)Thr37-Leu645 | 0 | 0.8 | 1 |
| (Thr)Ser38-Leu645 | 0 | 0 | 0 |
| (Ser)Asp39-Leu645 | 0 | 0 | 0 |
| (Val)Ser41-Leu645 | 0 | 0 | 0 |
| (Ser)Ser42-Leu645 | 0 | 0 | 0 |
| (Tyr)Leu44-Leu645 | 0 | 0 | 0 |
| (Lys)Glu51-Leu645 | 5.5 | 4.6 | 7 |

TABLE 2-continued

Fermentation broth B688 of ymp1 KO strain of SMD1163_pmt4 (1:40)

| Sequence | 0 hr | 24 hr | 48 hr |
| --- | --- | --- | --- |
| (Ala)Trp55-Leu645 | 0 | 0 | 0 |
| (Trp)Leu56-Leu645 | 0 | 0 | 0 |

Deletion of the yps1 protease from SMD1163 pmt4 (B805) did not remove any cleavage sites but decreases the amount cleaved at the Lys50/Glu51 site (Table 3).

TABLE 3

Fermentation broth B805 of yps1 KO strain of SMD1163_pmt4 (1:40)

| Sequence | 0 hr | 24 hr | 48 hr | 5 day |
| --- | --- | --- | --- | --- |
| His1-Leu645 | 100 | 73.6 | 37.3 | 6 |
| (Trp)Leu26-Leu645 | 0 | 1.6 | 1.9 | 2.3 |
| (Leu)Val27-Leu645 | 0 | 0 | 0 | 0 |
| (Lys)Gly29-Leu645 | 0 | 4.9 | 5.6 | 2.7 |
| (Phe)Thr37-Leu645 | 0 | 10 | 27.1 | 41 |
| (Thr)Ser38-Leu645 | 0 | 0 | 0 | 0 |
| (Ser)Asp39-Leu645 | 0 | 5.5 | 16 | 28 |
| (Val)Ser41-Leu645 | 0 | 0 | 0 | 0 |
| (Ser)Ser42-Leu645 | 0 | 1 | 2.6 | 4.2 |
| (Tyr)Leu44-Leu645 | 0 | 2.3 | 5.6 | 9 |
| (Lys)Glu51-Leu645 | 0 | 1.1 | 2 | 3.1 |
| (Ala)Trp55-Leu645 | 0 | 0 | 1.9 | 3.8 |
| (Trp)Leu56-Leu645 | 0 | 0 | 0 | 0 |

When Ymp1 and Yps1 proteases were both deleted from SMD1163_pmt4 (B803), the cleavage was significantly reduced and only occurred at Lys28/Gly29 (Table 4)

TABLE 4

Fermentation broth B803 of ymp1/yps1 KO strain of SMD1163_pmt4 (1:40)

| Sequence | 0 hr | 24 hr | 48 hr | 5 day |
| --- | --- | --- | --- | --- |
| His1-Leu645 | 100 | 94.5 | 89.4 | 73.1 |
| (Trp)Leu26-Leu645 | 0 | 0 | 0 | 0 |
| (Leu)Val27-Leu645 | 0 | 0 | 0 | 0 |
| (Lys)Gly29-Leu645 | 0 | 5.5 | 10.6 | 26.9 |
| (Phe)Thr37-Leu645 | 0 | 0 | 0 | 0 |
| (Thr)Ser38-Leu645 | 0 | 0 | 0 | 0 |
| (Ser)Asp39-Leu645 | 0 | 0 | 0 | 0 |
| (Val)Ser41-Leu645 | 0 | 0 | 0 | 0 |
| (Ser)Ser42-Leu645 | 0 | 0 | 0 | 0 |
| (Tyr)Leu44-Leu645 | 0 | 0 | 0 | 0 |
| (Lys)Glu51-Leu645 | 0 | 0 | 0 | 0 |
| (Ala)Trp55-Leu645 | 0 | 0 | 0 | 0 |
| (Trp)Leu56-Leu645 | 0 | 0 | 0 | 0 |

Individual knockout of ymp2, ymp3 was made in SMD1163. Shake flask inductions were performed on these knockout strains as well as SMD1163 control and culture supernatants samples were taken at 24 hours post induction. Protein standard described by SEQ ID NO:1 was incubated with these samples at 30° C. for 24 hour and analyzed by SDS PAGE gel.

Figure 9:
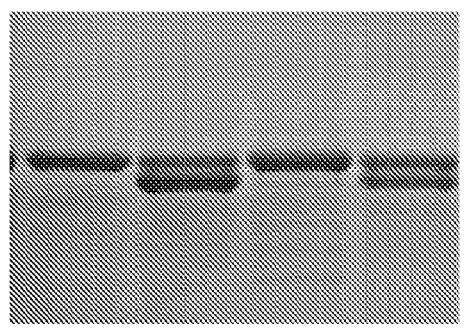
FIG. 9: Buffer stability study of ymp1, ymp3 mutant strains

From the PAGE analysis the deletion of ymp3 significantly decreased cleavage of the protein standard, but the ymp2 deletion has less effect on the proteolysis (See FIG. 9).

TABLE 5

| Gene | Description | Host | Protease def. | Evaluation |
|---|---|---|---|---|
| PEP4 | Aspartyl protease | X-33 | pep4 | Reduced heterologous proteolysis |
| PRB1 | Serine protease | X-33 pep4 | pep4, prb1 | Reduced heterologous proteolysis |
| YPS1 | Aspartyl protease | X-33 pep4 | pep4, ysp1 | Reduced heterologous proteolysis |
| YPS2 | secreted Aspartyl protease | SMD1163 | pep4, prb1, yps2 | Reduced heterologous proteolysis |
| YMP1 (SEQ ID NO: 4) | secreted serine protease | SMD1163 | pep4, prb1, ymp1 | Reduced heterologous proteolysis |
| DAP2 | DPP IV like endoprotease | SMD1163 | pep4, prb1, dap2 | No change proteolysis |
| GRH1 | Serine protease | SMD1163_clone6 | pep4, prb1, grh1 | No change proteolysis |
| PRD1 | metalloendopeptase | SMD1163_c16 [PDI] | pep4, prb1, prd1 | No change proteolysis |
| YSP3 | secreted serine protease | SMD1163_c16 [PDI] | pep4, prb1, ysp3 | No change proteolysis |
| PRB2 | Prb1 like Serine protease | SMD1163_c16 [PDI] | pep4, prb1, prb2 | — |
| PRB3 | Prb1 like Serine protease | SMD1163_clone6 | pep4, prb1, prb3 | No change proteolysis |
| YMP2 (SEQ ID NO: 6) | Arg/Ala aminopeptidase like | SMD1163 | pep4, prb1, ymp2 | Moderate reduction of heterologous proteolysis |
| YMP3 (SEQ ID NO: 8) | Leu aminopeptidase like | SMD1163 | pep4, prb1, ymp3 | Reduced heterologous proteolysis |
| PPC1 (SEQ ID NO: 10) | CPY like carboxypeptase | SMD1163_cl6 | pep4, prb1, ppc1 | — |
| PPC2 (SEQ ID NO: 12) | CPY like carboypeptase | SMD1163_cl6 | pep4, prb1, ppc2 | — |
| PPB1 (SEQ ID NO: 14) | Vacuolar protease B like | SMD1163_cl6 | pep4, prb1, ppb1 | — |

Six polypeptides are identified here, Pep4, Prb1, Yps1, Yps2 and newly discovered Ymp1, Ymp3, in *Pichia* that are responsible for the heterologous polypeptide (SEQ ID NO:1) degradation. Genetic knockout of these genes can significantly improve the productivity of the heterologous protein expression.

Example 4—Mannosyltransferase Knockouts

When the heterologous polypeptide (SEQ ID NO:1) produced from *Pichia* wild-type strain GS115 was analyzed by LC/MS, multiple 162 Da mass increase isoforms were observed. Further analysis using multiple enzyme digestion and LC/MS demonstrated that glycosylation occurred in the HSA moiety, and the results were confirmed using Edman sequencing and carbohydrate composition analysis (data not shown). Carbohydrate composition analysis confirmed that these modifications were caused by O-mannose glycosylation, which is a common post-translational modification of proteins produced in *Pichia pastoris*.

Figure 10:
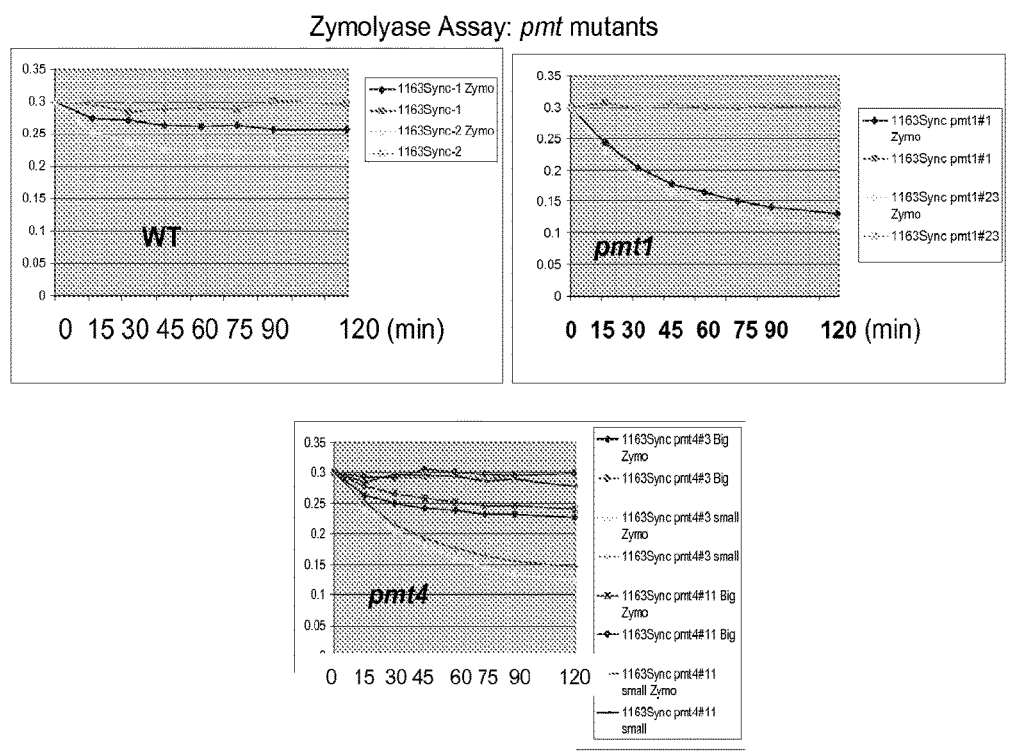
FIG. 10: Zymolyase assay results for wild type (WT), pmt1 and pmt4 *Pichia* mutants

Mannosyltransferase knockouts of *Pichia* strains were made using the same methods described in Example 2 for protease knockouts. Namely, a KanMX expression cassette was inserted in one of these genes responsible for glycosylation in yeast: OCH1, PMT1, PMT2, and PMT4. Knockout strains were transformed with a vector capable of expressing SEQ ID NO:1. The phenotypic changes of these knockout strains were demonstrated using the Zymolyase sensitivity assay (FIG. 10). In this experiment, exponentially growing yeast culture was diluted to OD600=0.3 in YPD supplemented with 5 U/ml of Zymolyase. The cultures were incubated in room temperature with gentle shaking Samples were collected at every 15 minutes for 2 hours and OD600 measurement was performed as an indicator of cell death.

Mannosyltransferase genes are essential for full cell wall integrity. pmt1 and pmt4 knockout strains may have partial or incomplete cell walls, which may result in enhanced sensitivity to Zymolyase treatment. The data showed that both pmt1 and pmt4 mutants died quickly with Zymolyase treatment.

Figure 11:
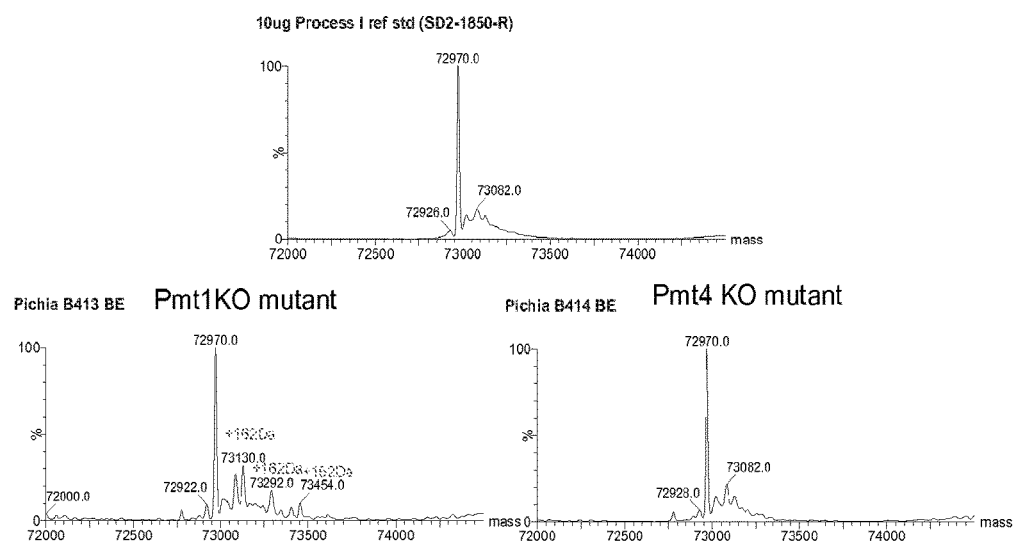
FIG. 11: Glycosylation analysis of heterologous protein (SEQ ID NO:1) from pmt4 mutant strain

Heterologous protein was evaluated for glycosylation comparing heterologous production in genetically modified strains with wild type strains. Summary results for knockouts are presented in Table 6 below. Also see FIG. 11. Results showed that Pmt4 is solely responsible for HSA glycosylation in *Pichia*. A pmt4 single knockout strain can produce glycosylation-free human HSA.

TABLE 6

| Gene | Description | Host | Protease def. | Evaluation |
|---|---|---|---|---|
| OCH1 | mannosyltransferase | SMD1163 | pep4, prb1, och1 | no change in glycosylation |
| PMT1 | mannosyltransferase | SMD1163 | pep4, prb1, pmt1 | no change in glycosylation |
| PMT2 | mannosyltransferase | SMD1163 | pep4, prb1, pmt2 | No clean KO |
| PMT4 | mannosyltransferase | SMD1163 | pep4, prb1, pmt4 | Glycosylation free |

Example 5—Co-Expression with Chaperon Proteins

Several chaperon proteins could be co-expressed with heterologous protein in a host cell to increase heterologous protein production. Examples of chaperon proteins that may be co-expressed with heterologous protein in yeast to increase heterologous production are presented in Table 7 below.

TABLE 7

| GENE | Protein name | Species of origin |
| --- | --- | --- |
| HAC1 | bZip transcription factor | S. cerevisiae |
| KAR2 | Binding protein BiP | S. cerevisiae |
| EUG | Homolog of PDI | S. cerevisiae |
| JEM1 | DnaJ-like protein of the ER Membrane 1 | Pichia & S. cerevisiae |
| CUP5 | Proteolipid subunit of the V-ATPase | Pichia & S. cerevisiae |
| KIN2 | serine/threonine protein kinase | Pichia & S. cerevisiae |
| SSA4 | heat shock protein | Pichia & S. cerevisiae |
| SSE1 | heat shock protein | Pichia & S. cerevisiae |
| HSP26 | 26-kDa heat shock protein | S. cerevisiae |

The invention claimed is:

1. A genetically modified *Pichia pastoris* strain of wild type X-33 or SMD1163, wherein a nucleic acid sequence encoding a YMP1 secreted serine protease having the nucleic acid sequence of SEQ ID NO: 3 is deleted, mutated or disrupted within wild type X-33 or SMD1163 to produce a reduced amount of activity or no activity of the YMP1 secreted serine protease compared with the wild type strain, and wherein the modified *Pichia pastoris* strain has reduced proteolysis and/or glycosylation.

2. The genetically modified *Pichia pastoris* strain of claim 1, further comprising knocked-out PEP4 and PRB1 genes, to produce a reduced amount of activity or no activity of aspartyl protease, and serine protease compared with the wild type strain.

* * * * *

SEQUENCE LISTING

```
<160> NUMBER OF SEQ ID NOS: 15

<210> SEQ ID NO 1
<211> LENGTH: 645
<212> TYPE: PRT
<213> ORGANISM: Artificial Sequence
<220> FEATURE:
<223> OTHER INFORMATION: Homo Sapiens

<400> SEQUENCE: 1

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg His Gly
            20                  25                  30

Glu Gly Thr Phe Thr Ser Asp Val Ser Ser Tyr Leu Glu Gly Gln Ala
        35                  40                  45

Ala Lys Glu Phe Ile Ala Trp Leu Val Lys Gly Arg Asp Ala His Lys
    50                  55                  60

Ser Glu Val Ala His Arg Phe Lys Asp Leu Gly Glu Glu Asn Phe Lys
65                  70                  75                  80

Ala Leu Val Leu Ile Ala Phe Ala Gln Tyr Leu Gln Gln Cys Pro Phe
                85                  90                  95

Glu Asp His Val Lys Leu Val Asn Glu Val Thr Glu Phe Ala Lys Thr
            100                 105                 110

Cys Val Ala Asp Glu Ser Ala Glu Asn Cys Asp Lys Ser Leu His Thr
        115                 120                 125

Leu Phe Gly Asp Lys Leu Cys Thr Val Ala Thr Leu Arg Glu Thr Tyr
    130                 135                 140

Gly Glu Met Ala Asp Cys Cys Ala Lys Gln Glu Pro Glu Arg Asn Glu
145                 150                 155                 160

Cys Phe Leu Gln His Lys Asp Asp Asn Pro Asn Leu Pro Arg Leu Val
                165                 170                 175

Arg Pro Glu Val Asp Val Met Cys Thr Ala Phe His Asp Asn Glu Glu
            180                 185                 190

Thr Phe Leu Lys Lys Tyr Leu Tyr Glu Ile Ala Arg Arg His Pro Tyr
        195                 200                 205

Phe Tyr Ala Pro Glu Leu Leu Phe Phe Ala Lys Arg Tyr Lys Ala Ala
    210                 215                 220

Phe Thr Glu Cys Cys Gln Ala Ala Asp Lys Ala Ala Cys Leu Leu Pro
225                 230                 235                 240

Lys Leu Asp Glu Leu Arg Asp Glu Gly Lys Ala Ser Ser Ala Lys Gln
                245                 250                 255
```

-continued

```
Arg Leu Lys Cys Ala Ser Leu Gln Lys Phe Gly Arg Ala Phe Lys
            260                 265                 270

Ala Trp Ala Val Ala Arg Leu Ser Gln Arg Phe Pro Lys Ala Glu Phe
        275                 280                 285

Ala Glu Val Ser Lys Leu Val Thr Asp Leu Thr Lys Val His Thr Glu
    290                 295                 300

Cys Cys His Gly Asp Leu Leu Glu Cys Ala Asp Asp Arg Ala Asp Leu
305                 310                 315                 320

Ala Lys Tyr Ile Cys Glu Asn Gln Asp Ser Ile Ser Ser Lys Leu Lys
                325                 330                 335

Glu Cys Cys Glu Lys Pro Leu Leu Glu Lys Ser His Cys Ile Ala Glu
            340                 345                 350

Val Glu Asn Asp Glu Met Pro Ala Asp Leu Pro Ser Leu Ala Ala Asp
        355                 360                 365

Phe Val Glu Ser Lys Asp Val Cys Lys Asn Tyr Ala Glu Ala Lys Asp
    370                 375                 380

Val Phe Leu Gly Met Phe Leu Tyr Glu Tyr Ala Arg Arg His Pro Asp
385                 390                 395                 400

Tyr Ser Val Val Leu Leu Leu Arg Leu Ala Lys Thr Tyr Glu Thr Thr
                405                 410                 415

Leu Glu Lys Cys Cys Ala Ala Ala Asp Pro His Glu Cys Tyr Ala Lys
            420                 425                 430

Val Phe Asp Glu Phe Lys Pro Leu Val Glu Glu Pro Gln Asn Leu Ile
        435                 440                 445

Lys Gln Asn Cys Glu Leu Phe Glu Gln Leu Gly Glu Tyr Lys Phe Gln
    450                 455                 460

Asn Ala Leu Leu Val Arg Tyr Thr Lys Lys Val Pro Gln Val Ser Thr
465                 470                 475                 480

Pro Thr Leu Val Glu Val Ser Arg Asn Leu Gly Lys Val Gly Ser Lys
                485                 490                 495

Cys Cys Lys His Pro Glu Ala Lys Arg Met Pro Cys Ala Glu Asp Tyr
            500                 505                 510

Leu Ser Val Val Leu Asn Gln Leu Cys Val Leu His Glu Lys Thr Pro
        515                 520                 525

Val Ser Asp Arg Val Thr Lys Cys Cys Thr Glu Ser Leu Val Asn Arg
    530                 535                 540

Arg Pro Cys Phe Ser Ala Leu Glu Val Asp Glu Thr Tyr Val Pro Lys
545                 550                 555                 560

Glu Phe Asn Ala Glu Thr Phe Thr Phe His Ala Asp Ile Cys Thr Leu
                565                 570                 575

Ser Glu Lys Glu Arg Gln Ile Lys Lys Gln Thr Ala Leu Val Glu Leu
            580                 585                 590

Val Lys His Lys Pro Lys Ala Thr Lys Glu Gln Leu Lys Ala Val Met
        595                 600                 605

Asp Asp Phe Ala Ala Phe Val Glu Lys Cys Cys Lys Ala Asp Asp Lys
    610                 615                 620

Glu Thr Cys Phe Ala Glu Glu Gly Lys Lys Leu Val Ala Ala Ser Gln
625                 630                 635                 640

Ala Ala Leu Gly Leu
                645

<210> SEQ ID NO 2
<211> LENGTH: 31
```

```
<212> TYPE: PRT
<213> ORGANISM: Homo Sapiens
<220> FEATURE:
<221> NAME/KEY: VARIANT
<222> LOCATION: 31
<223> OTHER INFORMATION: Xaa = Any Amino Acid

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 3
<211> LENGTH: 5115
<212> TYPE: DNA
<213> ORGANISM: Pichia Pastoris

<400> SEQUENCE: 3
atgttcctca aaagtctcct tagttttgcg tctatcctaa cgctttgcaa ggcctgggat      60
ctggaagatg tacaagatgc accaaagatc aaggtaatg aagtacccgg tcgctatatc     120
attgagtatg aagaagcttc cacttcagca tttgctaccc aactgagagc tgggggatat     180
gactttaaca tccaatacga ctactcaact ggttcccttt tcaacggagc atctgttcaa     240
atcagcaacg ataacaaaac cactttccag gatttgcaaa gttgcgtgc agtcaaaaat      300 gtttacccag ctactctcat tacattagat gaaacatttg agcttgctga cacgaagcca     360
tggaaccctc atggaattac cggtgtcgat tctttgcatg agcaaggata tactggtagt     420
ggtgttgtta ttgcagttat cgatactggt gttgactata cacaccctgc tctgggtggt     480
ggtatcggag ataatttccc tatcaaagct ggttatgatt tgtcttccgg tgatggtgtc     540
atcacgaatg atcctatgga ttgtgacggt catggtacct tgtatcctc catcattgtt      600 gcaaataaca agatatggt tggtgttgca ccagatgctc agattgtcat gtacaaagtg     660
ttcccctgtt ctgatagtac ttcgactgac atagttatgg cgggtatgca aaaggcctat     720
gatgatggtc acaagattat ttcgctatca ctgggatctg actcgggggtt ttccagtact     780 ccagcttcct taatggccag caggattgct caagacagag ttgttttggt ggctgctggt     840
aactctggag aacttggtcc attctatgcc tcctcccctg cttctgggaa caagtcatt      900 tcagttggat ctgttcaaaa cgaacaatgg acaacctttc agtaacctt tacctcttca     960 aacggtgaat caaggggtttt tccttacctc gcttacaatg tgcacagat tggatttgat    1020 gccgagcttg aggttgattt taccgaagaa agaggatgcg tctatgaacc agagatctcc    1080
gcagataatg cgaataaagc tattttgtta agaagggggcg tcggctgtgt tgaaaacttg    1140
gaattcaatt tattgtctgt ggctggttac aaggcttact tcttgtacaa ctcattttca    1200
agaccatgga gtctcttgaa tatttctcca ctgattgagc tagacaacgc ttactctctt    1260
gttgaagagg aagttggaat atgggtgaaa acccaaatcg acgccggtaa caccgtcaag    1320
ttaaaggtga gcacgagtga ccaaatgttg ccatctgata agagtatttt gggagttgga    1380
aagatggatt attactcctc tcaaggacct gcttatgagc ttgaatttttt cccaacgata    1440 tccgctccag gtggagacag ttggggcgct tggcccggtg gcaatacgg tgttgcctca    1500 ggaacaagtt ttgcttgccc ctatgttgca ggtcttacag ctctttatga atcgcagttt    1560
ggaattcaag atcccagga ctatgtgaga aaattagtct ccacagctac cgatcttcaa    1620
ttatttgact ggaacgcagt gaaacttgag acctctatga atgctccact tattcaacag    1680
```

```
ggagctggtc tagtgaacgc tcttggtttg tttgagacta agactgtgat cgtgtctgct    1740
ccttatttgg agctcaatga caccatcaat agagccagtg agtataccat tcaaattaag    1800
aatgagaact ctgagactat tacctatcaa gttgttcacg ttccgggaac tactgtctac    1860
tctagatcag cttctgggaa catcccatac ctggtcaatc aagattttgc accttacggt    1920
gatagtgatg ctgcgacagt tgctctatcc acagaagagt tggttttggg accaggagaa    1980
gttggtgaag tcactgtgat cttctctaca gaagaaattg atcaagaaac tgctccaatt    2040
attcagggta agattacatt ttatggtgat gtcataccga ttgctgttcc ttatatggga    2100
gttgaagttg atattcattc ctgggagcct ctcattgaga ggcctttatc agtgagaatg    2160
tatttggatg atggttcctt agcatatgtt gatgatgatc ctgattatga gttcaatgtg    2220
tatgactggg attctcctag attttatttt aacctgagat atgcaaccaa agaagtatcg    2280
attgacttgg tgcaccctga ttatagcatt gagaacgact acgaatggcc tttagtttcc    2340
ggacacaaca actattatgg tcccgtggga tacgactacg attataccctc gggtcaagcc    2400 tttttgcctc gttactttca acaacgtatt aacgaacttg gatatctttc tttttccaga    2460
tttgctaact tttctgtagt tcctgctggt gaatacaaag ctctatttag agttttgcta    2520
ccatatggag actttggaa caaagaagac tggcaattgt ttgaatcccc agtgtttaac    2580
gtcctcgctc caccgaatga agaaaacact actgaagagc caactgagga atccagcgag    2640
gagcctaccg aagagtcaac gtctgagtca actgaagagc cctcttctga gtcaactgag    2700
aaatctagcg aggtgccaac tgaagaaatt actgaagatg caacatccac aattgatgat    2760
gatgaagcat ccaccgaaag ctctactgaa gaaccaagtg ctcagcccac cggtccttac    2820
tctgatttga ctgtcggtga ggccattacc gacgttagtg tcaccagttt gaggacaact    2880
gaagcatttg gatacacttc cgactggttg gttgtgtctt tcactttcaa cactactgac    2940
agagatatta ctctcccacc ttacgctgtt gtacaagtaa ctatcccaaa tgaacttcaa    3000
ttcattgctc atccagaata cgccccatac cttgagccct cattgcaagt tttctacact    3060
aagaatgaaa gattaattat gactagtcag ttcaactacg acaccagagt catcgacttc    3120
aagtttgaca atcgagacca agtaataact caagtggagg gagttgttta tttcacgatg    3180
aaactagaac aagatttcat ttctgcattg gccccaggtg aatacgattt tgaatttcat    3240
acatccgttg attcttatgc ttcgaccttt gactttattc cattgattag atccgagcca    3300
atcaaattga tagcaggtgc accagacgaa gttgaatggt ttattgatat tccaagtgca    3360
tacagcgatt tggcaacgat agatattagt tctgatatcg atactaatga taatttgcag    3420
cagtacttct atgattgctc aaagctcaag tacactattg gaaaagagtt tgatcagtgg    3480 ggtaattttta cagctggatc agatggtaac caatacagca ataccaccga tgggtatgtt    3540
ccaattactg attctaccgg ctctccagta gctgaagttc aatgtttaat ggaaagtatc    3600
tcattgagtt tcacaaatac tcttgctgag gatgaagtat tgagagttgt tcttcactct    3660 tctgcgtttta gacgtggttc attcaccatg gccaacgtgg taaacgttga cattacagct    3720
ggtggattgg caaaaagaga actcttctct tatatattgg atgaaaatta ctatgctagt    3780
actggatctg aggggttggc atttgacgta tttgaagttg ctgatcaggt cgaggagcca    3840
actgaggagt caacctcaga ggaatctact gaacaggaaa cttccaccga ggaacctacc    3900
gaggaatcaa ctgaacctac tgaggaatct acccaggaac ctactgaaga gcccaccgac    3960
gagcctactt ctgagtcaac tgaggaacct tctgaggagc aacttctgaa cgatctctca    4020
attgacccaa ctgctgtacc taccgatgaa cctactgaag agccaactga ggagcctact    4080
```

```
tctgagtcaa ctgaggaacc ttctgaggag ccaacttctg acgatctctc aattgaccca    4140
actgctgtac ctaccgatga acctactgaa gagccaactg aggagcctac ttctgagtca    4200
actgaggaac cttctgagga gccaacttct gacgatctct caattgaccc aactgctgta    4260
cctaccgatg aacctactga agagccaact gaggagccga cctctgagac taccgatgat    4320
ccatcgatag cacctactgc tgtgccaact tccgacacat cttctggaca atcggtggtt    4380
actcaaaaca ctacagtcac tcagactacc atcacttcag tctgtaatgt ttgtgctgag    4440 accctgtaa caatcactta cactgcacca gttgtgacta agccagtttc ttacaccacc    4500
gttacttcag tttgccatgt atgtgcagag acaccaatca cagttacctt gacgttgcca    4560
tgtgaaaccg aagacgtgac aaagactgcc ggccctaaga ctgtcactta caccgaagtt    4620
tgcaactcct gtgctgacaa gcctatcact tacacctaca tcgctccaga gtacactcaa    4680
ggtgccgaac gtacaacagt tacatcggtt tgcaacgttt gtgctgagac acctgtaacg    4740
ctaacataca ctgcgccgaa agccagtcgt catacagttc cttcacaata ttcaagtgcc    4800
ggagagctca tttcatccaa ggggatcacg attcctactg ttcctgcccg tccaactggt    4860
acttatagta agtctgttga cactagccaa cgtacactcg ctaccattac aaaatcttca    4920
gatgagtcta acactgttac cactactcaa gccacacaag ttttgagcgg tgaatccagt    4980
ggaattcaag ctgcttcaaa cagcacgagc atctcagctc caactgtcac tacagctggg    5040
aacgagaact ctggatctag attttcgttt gctggactat tcacagttct gcctcttatc    5100
ttgttcgtta tataa                                                    5115
```

<210> SEQ ID NO 4
<211> LENGTH: 1703
<212> TYPE: PRT
<213> ORGANISM: Pichia Pastoris

<400> SEQUENCE: 4

```
Met Phe Leu Lys Ser Leu Leu Ser Phe Ala Ser Ile Leu Thr Leu Cys
1               5                   10                  15

Lys Ala Trp Asp Leu Glu Asp Val Gln Asp Ala Pro Lys Ile Lys Gly
            20                  25                  30

Asn Glu Val Pro Gly Arg Tyr Ile Ile Glu Tyr Glu Glu Ala Ser Thr
        35                  40                  45

Ser Ala Phe Ala Thr Gln Leu Arg Ala Gly Gly Tyr Asp Phe Asn Ile
    50                  55                  60

Gln Tyr Asp Tyr Ser Thr Gly Ser Leu Phe Asn Gly Ala Ser Val Gln
65                  70                  75                  80

Ile Ser Asn Asp Asn Lys Thr Thr Phe Gln Asp Leu Gln Ser Leu Arg
                85                  90                  95

Ala Val Lys Asn Val Tyr Pro Ala Thr Leu Ile Thr Leu Asp Glu Thr
            100                 105                 110

Phe Glu Leu Ala Asp Thr Lys Pro Trp Asn Pro His Gly Ile Thr Gly
        115                 120                 125

Val Asp Ser Leu His Glu Gln Gly Tyr Thr Gly Ser Gly Val Val Ile
    130                 135                 140

Ala Val Ile Asp Thr Gly Val Asp Tyr Thr His Pro Ala Leu Gly Gly
145                 150                 155                 160

Gly Ile Gly Asp Asn Phe Pro Ile Lys Ala Gly Tyr Asp Leu Ser Ser
                165                 170                 175

Gly Asp Gly Val Ile Thr Asn Asp Pro Met Asp Cys Asp Gly His Gly
```

```
                   180             185              190
Thr Phe Val Ser Ser Ile Ile Val Ala Asn Asn Lys Asp Met Val Gly
            195              200             205

Val Ala Pro Asp Ala Gln Ile Val Met Tyr Lys Val Phe Pro Cys Ser
            210             215              220

Asp Ser Thr Ser Thr Asp Ile Val Met Ala Gly Met Gln Lys Ala Tyr
225             230              235                          240

Asp Asp Gly His Lys Ile Ile Ser Leu Ser Leu Gly Ser Asp Ser Gly
                245              250             255

Phe Ser Ser Thr Pro Ala Ser Leu Met Ala Ser Arg Ile Ala Gln Asp
            260             265             270

Arg Val Val Leu Val Ala Gly Asn Ser Gly Glu Leu Gly Pro Phe
            275             280             285

Tyr Ala Ser Ser Pro Ala Ser Gly Lys Gln Val Ile Ser Val Gly Ser
            290             295             300

Val Gln Asn Glu Gln Trp Thr Thr Phe Pro Val Thr Phe Thr Ser Ser
305             310             315                          320

Asn Gly Glu Ser Arg Val Phe Pro Tyr Leu Ala Tyr Asn Gly Ala Gln
                325             330             335

Ile Gly Phe Asp Ala Glu Leu Glu Val Asp Phe Thr Glu Glu Arg Gly
                340             345             350

Cys Val Tyr Glu Pro Glu Ile Ser Ala Asp Asn Ala Asn Lys Ala Ile
                355             360             365

Leu Leu Arg Arg Gly Val Gly Cys Val Glu Asn Leu Glu Phe Asn Leu
            370             375             380

Leu Ser Val Ala Gly Tyr Lys Ala Tyr Phe Leu Tyr Asn Ser Phe Ser
385             390             395                          400

Arg Pro Trp Ser Leu Leu Asn Ile Ser Pro Leu Ile Glu Leu Asp Asn
                405             410             415

Ala Tyr Ser Leu Val Glu Glu Val Gly Ile Trp Val Lys Thr Gln
            420             425             430

Ile Asp Ala Gly Asn Thr Val Lys Leu Lys Val Ser Thr Ser Asp Gln
                435             440             445

Met Leu Pro Ser Asp Lys Glu Tyr Leu Gly Val Gly Lys Met Asp Tyr
            450             455             460

Tyr Ser Ser Gln Gly Pro Ala Tyr Glu Leu Glu Phe Phe Pro Thr Ile
465             470             475                          480

Ser Ala Pro Gly Gly Asp Ser Trp Gly Ala Trp Pro Gly Gly Gln Tyr
                485             490             495

Gly Val Ala Ser Gly Thr Ser Phe Ala Cys Pro Tyr Val Ala Gly Leu
            500             505             510

Thr Ala Leu Tyr Glu Ser Gln Phe Gly Ile Gln Asp Pro Gln Asp Tyr
            515             520             525

Val Arg Lys Leu Val Ser Thr Ala Thr Asp Leu Gln Leu Phe Asp Trp
            530             535             540

Asn Ala Val Lys Leu Glu Thr Ser Met Asn Ala Pro Leu Ile Gln Gln
545             550             555                          560

Gly Ala Gly Leu Val Asn Ala Leu Gly Leu Phe Glu Thr Lys Thr Val
                565             570             575

Ile Val Ser Ala Pro Tyr Leu Glu Leu Asn Asp Thr Ile Asn Arg Ala
                580             585             590

Ser Glu Tyr Thr Ile Gln Ile Lys Asn Glu Asn Ser Glu Thr Ile Thr
                595             600             605
```

-continued

Tyr Gln Val Val His Val Pro Gly Thr Thr Val Tyr Ser Arg Ser Ala
    610                 615                 620

Ser Gly Asn Ile Pro Tyr Leu Val Asn Gln Asp Phe Ala Pro Tyr Gly
625                 630                 635                 640

Asp Ser Asp Ala Ala Thr Val Ala Leu Ser Thr Glu Glu Leu Val Leu
                645                 650                 655

Gly Pro Gly Glu Val Gly Glu Val Thr Val Ile Phe Ser Thr Glu Glu
                660                 665                 670

Ile Asp Gln Glu Thr Ala Pro Ile Ile Gln Gly Lys Ile Thr Phe Tyr
        675                 680                 685

Gly Asp Val Ile Pro Ile Ala Val Pro Tyr Met Gly Val Glu Val Asp
    690                 695                 700

Ile His Ser Trp Glu Pro Leu Ile Glu Arg Pro Leu Ser Val Arg Met
705                 710                 715                 720

Tyr Leu Asp Asp Gly Ser Leu Ala Tyr Val Asp Asp Pro Asp Tyr
                725                 730                 735

Glu Phe Asn Val Tyr Asp Trp Asp Ser Pro Arg Phe Tyr Phe Asn Leu
                740                 745                 750

Arg Tyr Ala Thr Lys Glu Val Ser Ile Asp Leu Val His Pro Asp Tyr
        755                 760                 765

Ser Ile Glu Asn Asp Tyr Glu Trp Pro Leu Val Ser Gly His Asn Asn
    770                 775                 780

Tyr Tyr Gly Pro Val Gly Tyr Asp Tyr Asp Tyr Thr Ser Gly Gln Ala
785                 790                 795                 800

Phe Leu Pro Arg Tyr Phe Gln Gln Arg Ile Asn Glu Leu Gly Tyr Leu
                805                 810                 815

Ser Phe Ser Arg Phe Ala Asn Phe Ser Val Val Pro Ala Gly Glu Tyr
            820                 825                 830

Lys Ala Leu Phe Arg Val Leu Leu Pro Tyr Gly Asp Phe Trp Asn Lys
        835                 840                 845

Glu Asp Trp Gln Leu Phe Glu Ser Pro Val Phe Asn Val Leu Ala Pro
    850                 855                 860

Pro Asn Glu Glu Asn Thr Thr Glu Glu Pro Thr Glu Glu Ser Ser Glu
865                 870                 875                 880

Glu Pro Thr Glu Glu Ser Thr Ser Glu Ser Thr Glu Glu Pro Ser Ser
                885                 890                 895

Glu Ser Thr Glu Lys Ser Ser Glu Val Pro Thr Glu Glu Ile Thr Glu
            900                 905                 910

Asp Ala Thr Ser Thr Ile Asp Asp Glu Ala Ser Thr Glu Ser Ser
        915                 920                 925

Thr Glu Glu Pro Ser Ala Gln Pro Thr Gly Pro Tyr Ser Asp Leu Thr
    930                 935                 940

Val Gly Glu Ala Ile Thr Asp Val Ser Val Thr Ser Leu Arg Thr Thr
945                 950                 955                 960

Glu Ala Phe Gly Tyr Thr Ser Asp Trp Leu Val Ser Phe Thr Phe
            965                 970                 975

Asn Thr Thr Asp Arg Asp Ile Thr Leu Pro Pro Tyr Ala Val Val Gln
            980                 985                 990

Val Thr Ile Pro Asn Glu Leu Gln Phe Ile Ala His Pro Glu Tyr Ala
        995                 1000                1005

Pro Tyr Leu Glu Pro Ser Leu Gln Val Phe Tyr Thr Lys Asn Glu Arg
    1010                1015                1020

```
Leu Ile Met Thr Ser Gln Phe Asn Tyr Asp Thr Arg Val Ile Asp Phe
1025                1030                1035                1040

Lys Phe Asp Asn Arg Asp Gln Val Ile Thr Gln Val Glu Gly Val Val
            1045                1050                1055

Tyr Phe Thr Met Lys Leu Glu Gln Asp Phe Ile Ser Ala Leu Ala Pro
            1060                1065                1070

Gly Glu Tyr Asp Phe Glu Phe His Thr Ser Val Asp Ser Tyr Ala Ser
            1075                1080                1085

Thr Phe Asp Phe Ile Pro Leu Ile Arg Ser Glu Pro Ile Lys Leu Ile
            1090                1095                1100

Ala Gly Ala Pro Asp Glu Val Glu Trp Phe Ile Asp Ile Pro Ser Ala
1105                1110                1115                1120

Tyr Ser Asp Leu Ala Thr Ile Asp Ile Ser Ser Asp Ile Asp Thr Asn
            1125                1130                1135

Asp Asn Leu Gln Gln Tyr Phe Tyr Asp Cys Ser Lys Leu Lys Tyr Thr
            1140                1145                1150

Ile Gly Lys Glu Phe Asp Gln Trp Gly Asn Phe Thr Ala Gly Ser Asp
            1155                1160                1165

Gly Asn Gln Tyr Ser Asn Thr Thr Asp Gly Tyr Val Pro Ile Thr Asp
            1170                1175                1180

Ser Thr Gly Ser Pro Val Ala Glu Val Gln Cys Leu Met Glu Ser Ile
1185                1190                1195                1200

Ser Leu Ser Phe Thr Asn Thr Leu Ala Glu Asp Glu Val Leu Arg Val
            1205                1210                1215

Val Leu His Ser Ser Ala Phe Arg Arg Gly Ser Phe Thr Met Ala Asn
            1220                1225                1230

Val Val Asn Val Asp Ile Thr Ala Gly Gly Leu Ala Lys Arg Glu Leu
            1235                1240                1245

Phe Ser Tyr Ile Leu Asp Glu Asn Tyr Tyr Ala Ser Thr Gly Ser Glu
            1250                1255                1260

Gly Leu Ala Phe Asp Val Phe Glu Val Ala Asp Gln Val Glu Glu Pro
1265                1270                1275                1280

Thr Glu Glu Ser Thr Ser Glu Glu Ser Thr Glu Gln Glu Thr Ser Thr
            1285                1290                1295

Glu Glu Pro Thr Glu Glu Ser Thr Glu Pro Thr Glu Glu Ser Thr Gln
            1300                1305                1310

Glu Pro Thr Glu Glu Pro Thr Asp Glu Pro Thr Ser Glu Ser Thr Glu
            1315                1320                1325

Glu Pro Ser Glu Glu Pro Thr Ser Asp Asp Leu Ser Ile Asp Pro Thr
            1330                1335                1340

Ala Val Pro Thr Asp Glu Pro Thr Glu Glu Pro Thr Glu Glu Pro Thr
1345                1350                1355                1360

Ser Glu Ser Thr Glu Glu Pro Ser Glu Thr Ser Asp Asp Leu Ser
            1365                1370                1375

Ile Asp Pro Thr Ala Val Pro Thr Asp Glu Pro Thr Glu Glu Pro Thr
            1380                1385                1390

Glu Glu Pro Thr Ser Glu Ser Thr Glu Glu Pro Ser Glu Glu Pro Thr
            1395                1400                1405

Ser Asp Asp Leu Ser Ile Asp Pro Thr Ala Val Pro Thr Asp Glu Pro
            1410                1415                1420

Thr Glu Glu Pro Thr Glu Glu Pro Thr Ser Glu Thr Thr Asp Asp Pro
1425                1430                1435                1440

Ser Ile Ala Pro Thr Ala Val Pro Thr Ser Asp Thr Ser Ser Gly Gln
```

```
                    1445                1450                1455
Ser Val Val Thr Gln Asn Thr Thr Val Thr Gln Thr Thr Ile Thr Ser
            1460                1465                1470

Val Cys Asn Val Cys Ala Glu Thr Pro Val Thr Ile Thr Tyr Thr Ala
        1475                1480                1485

Pro Val Val Thr Lys Pro Val Ser Tyr Thr Thr Val Thr Ser Val Cys
    1490                1495                1500

His Val Cys Ala Glu Thr Pro Ile Thr Val Thr Leu Thr Leu Pro Cys
1505                1510                1515                1520

Glu Thr Glu Asp Val Thr Lys Thr Ala Gly Pro Lys Thr Val Thr Tyr
            1525                1530                1535

Thr Glu Val Cys Asn Ser Cys Ala Asp Lys Pro Ile Thr Tyr Thr Tyr
        1540                1545                1550

Ile Ala Pro Glu Tyr Thr Gln Gly Ala Glu Arg Thr Thr Val Thr Ser
    1555                1560                1565

Val Cys Asn Val Cys Ala Glu Thr Pro Val Thr Leu Thr Tyr Thr Ala
1570                1575                1580

Pro Lys Ala Ser Arg His Thr Val Pro Ser Gln Tyr Ser Ser Ala Gly
            1585                1590                1595                1600

Glu Leu Ile Ser Ser Lys Gly Ile Thr Ile Pro Thr Val Pro Ala Arg
        1605                1610                1615

Pro Thr Gly Thr Tyr Ser Lys Ser Val Asp Thr Ser Gln Arg Thr Leu
    1620                1625                1630

Ala Thr Ile Thr Lys Ser Ser Asp Glu Ser Asn Thr Val Thr Thr
            1635                1640                1645

Gln Ala Thr Gln Val Leu Ser Gly Glu Ser Gly Ile Gln Ala Ala
        1650                1655                1660

Ser Asn Ser Thr Ser Ile Ser Ala Pro Thr Val Thr Thr Ala Gly Asn
1665                1670                1675                1680

Glu Asn Ser Gly Ser Arg Phe Ser Phe Ala Gly Leu Phe Thr Val Leu
            1685                1690                1695

Pro Leu Ile Leu Phe Val Ile
        1700

<210> SEQ ID NO 5
<211> LENGTH: 618
<212> TYPE: DNA
<213> ORGANISM: Pichia Pastoris

<400> SEQUENCE: 5
atggctccca gaacactacc agaagactta attccctccc tatacgactt gcacatctac      60
aacttccaac ccgaaaaaaa gacttatgat ggagacattg tcatccactt ggaggtgaag     120
gagcccactg atgaagtggt cttcaatgcc aaggatttgg aattgaaaga cgtacatgtc     180
ttccacaatg tcaacaagtc tgaaaacgaa atccccgtta aggagattgt tgataacgag     240
ctcatcacaa ttaagctcaa agagaaggtt acttccggaa cgttgctggt gaatatttcc     300
ttcaccggta acattcaatc tgataaaatt ggattttaca agggagacac agatgtggaa     360
ggaagagtca catacactac aaaccttacc actccaaatg ccaggttggc attcccatgt     420
cttgataaca tattgttgaa agctccattc aagttcggag taactgccaa tccaggacaa     480
ttagtgagtt ccatttttgga tctaagctct gaggctgacg tcttgaatga caatgacgat     540
gtgattggta cgagatacca ataccaagtg agtgagccaa tagccccagc tttactggag     600
tggaccattc atatttaa                                                   618
```

<210> SEQ ID NO 6
<211> LENGTH: 205
<212> TYPE: PRT
<213> ORGANISM: Pichia Pastoris

<400> SEQUENCE: 6

Met Ala Pro Arg Thr Leu Pro Glu Asp Leu Ile Pro Ser Leu Tyr Asp
1               5                   10                  15

Leu His Ile Tyr Asn Phe Gln Pro Glu Lys Lys Thr Tyr Asp Gly Asp
            20                  25                  30

Ile Val Ile His Leu Glu Val Lys Glu Pro Thr Asp Glu Val Val Phe
        35                  40                  45

Asn Ala Lys Asp Leu Glu Leu Lys Asp Val His Val Phe His Asn Val
    50                  55                  60

Asn Lys Ser Glu Asn Glu Ile Pro Val Lys Glu Ile Val Asp Asn Glu
65                  70                  75                  80

Leu Ile Thr Ile Lys Leu Lys Glu Lys Val Thr Ser Gly Thr Leu Leu
                85                  90                  95

Val Asn Ile Ser Phe Thr Gly Asn Ile Gln Ser Asp Lys Ile Gly Phe
            100                 105                 110

Tyr Lys Gly Asp Thr Asp Val Glu Gly Arg Val Thr Tyr Thr Thr Asn
        115                 120                 125

Leu Thr Thr Pro Asn Ala Arg Leu Ala Phe Pro Cys Leu Asp Asn Ile
    130                 135                 140

Leu Leu Lys Ala Pro Phe Lys Phe Gly Val Thr Ala Asn Pro Gly Gln
145                 150                 155                 160

Leu Val Ser Ser Ile Leu Asp Leu Ser Ser Glu Ala Asp Val Leu Asn
                165                 170                 175

Asp Asn Asp Asp Val Ile Gly Thr Arg Tyr Gln Tyr Gln Val Ser Glu
            180                 185                 190

Pro Ile Ala Pro Ala Leu Leu Glu Trp Thr Ile His Ile
        195                 200                 205

<210> SEQ ID NO 7
<211> LENGTH: 1233
<212> TYPE: DNA
<213> ORGANISM: Pichia Pastoris

<400> SEQUENCE: 7
atggtcaaac tcatatcaat tatagcccta gttcaacttg tctctgcgac aattgtacct      60
tggaatctcc agaacgtctt atctgacgtc catcacccct ctctccatct cttggattat     120
attcaatcct tgaagaacga ggtaatgttc gatggcgacg atcgcagaat aatcaagtta     180
ggcccccaag aataccgtat tatcactgaa aaagagaaat accagttgaa aacagagggg     240
atatcattta tcgatgtcac ctatcagcat ggagacaatg tagagctgct ctattccagt     300
gcgccagtta ccgttccaga ctatctttat ccgtccaatg atactttcca tttcaaacaa     360
gtaaattctt tgataggtga gattgacatt ggcagaatgc aggcgttttt gggaaggttc     420
tctagcttct ttacaagatt ttacaaatct gacaaggggt tgcagagttc tatctggtta     480
caaggtgaat tggttcaatt ggccttgaaa gatccatcga ggttcaatgt tactactgtg     540
gaacacccct tggaagcaga attctgccat ctttacgata tacggtgaaaa tgttgatcct     600 tcgaaaggaa aaggggacat tgtagtagtg ggatgccatc aagattccat aaacttgctt     660
ttccccaaca ttctccgtgc tccagggggct gatgatgatg atctggtgt aacttccaac     720

-continued

```
cttgaagcgc tcagaatcat agttgaaagt ggcctcaagt ttcacaatac agtagagttt    780 cactttatt  ctgccgaaga aggaggacta cttggctccc agcaaatttt cagctcgtat    840
agagctgcag aagagactgt tgttgctatg ctacaacagg acatgactgg atacatccaa    900
aaagctttag accacgggga atccgaccac ttcgggctaa tcactgacca tacaaacgca    960
aatctgaata gcttccttgc acttttaatc gatgcataca cttcaattcc ctacaaagaa   1020
accgaatgtg gtatgcctg  ctcagatcat agttctgcct ggaacatgg  ttatccatct   1080 gccatggtct ttgaaagtag ttttgcctac acaaatccct tcatccatag cacccaagac   1140
acaattgaca agatcaattt tccacatatg gcagagcatg tcaagttggt cctgggttac   1200
gttgtagagt tgggattaga acattttagg tga                                1233
```

<210> SEQ ID NO 8
<211> LENGTH: 410
<212> TYPE: PRT
<213> ORGANISM: Pichia Pastoris

<400> SEQUENCE: 8

```
Met Val Lys Leu Ile Ser Ile Ile Ala Leu Val Gln Leu Val Ser Ala
1               5                   10                  15

Thr Ile Val Pro Trp Asn Leu Gln Asn Val Leu Ser Asp Val His His
            20                  25                  30

Pro Ser Leu His Leu Leu Asp Tyr Ile Gln Ser Leu Lys Asn Glu Val
        35                  40                  45

Met Phe Asp Gly Asp Asp Arg Arg Ile Ile Lys Leu Gly Pro Gln Glu
    50                  55                  60

Tyr Arg Ile Ile Thr Glu Lys Glu Lys Tyr Gln Leu Lys Thr Glu Gly
65                  70                  75                  80

Ile Ser Phe Ile Asp Val Thr Tyr Gln His Gly Asp Asn Val Glu Leu
                85                  90                  95

Leu Tyr Ser Ser Ala Pro Val Thr Val Pro Asp Tyr Leu Tyr Pro Ser
            100                 105                 110

Asn Asp Thr Phe His Phe Lys Gln Val Asn Ser Leu Ile Gly Glu Ile
        115                 120                 125

Asp Ile Gly Arg Met Gln Ala Phe Leu Gly Arg Phe Ser Ser Phe Phe
    130                 135                 140

Thr Arg Phe Tyr Lys Ser Asp Lys Gly Leu Gln Ser Ser Ile Trp Leu
145                 150                 155                 160

Gln Gly Glu Leu Val Gln Leu Ala Leu Lys Asp Pro Ser Arg Phe Asn
                165                 170                 175

Val Thr Thr Val Glu His Pro Trp Lys Gln Asn Ser Ala Ile Phe Thr
            180                 185                 190

Ile Tyr Gly Glu Asn Val Asp Pro Ser Lys Gly Lys Gly Asp Ile Val
        195                 200                 205

Val Val Gly Cys His Gln Asp Ser Ile Asn Leu Phe Pro Asn Ile
    210                 215                 220

Leu Arg Ala Pro Gly Ala Asp Asp Gly Ser Gly Val Thr Ser Asn
225                 230                 235                 240

Leu Glu Ala Leu Arg Ile Val Glu Ser Gly Leu Lys Phe His Asn
                245                 250                 255

Thr Val Glu Phe His Phe Tyr Ser Ala Glu Glu Gly Gly Leu Leu Gly
            260                 265                 270

Ser Gln Gln Ile Phe Ser Ser Tyr Arg Ala Ala Glu Glu Thr Val Val
```

```
            275                 280                 285
Ala Met Leu Gln Gln Asp Met Thr Gly Tyr Ile Gln Lys Ala Leu Asp
    290                 295                 300

His Gly Glu Ser Asp His Phe Gly Leu Ile Thr Asp His Thr Asn Ala
305                 310                 315                 320

Asn Leu Asn Ser Phe Leu Ala Leu Leu Ile Asp Ala Tyr Thr Ser Ile
                325                 330                 335

Pro Tyr Lys Glu Thr Glu Cys Gly Tyr Ala Cys Ser Asp His Ser Ser
            340                 345                 350

Ala Leu Glu His Gly Tyr Pro Ser Ala Met Val Phe Glu Ser Ser Phe
        355                 360                 365

Ala Tyr Thr Asn Pro Phe Ile His Ser Thr Gln Asp Thr Ile Asp Lys
    370                 375                 380

Ile Asn Phe Pro His Met Ala Glu His Val Lys Leu Val Leu Gly Tyr
385                 390                 395                 400

Val Val Glu Leu Gly Leu Glu His Phe Arg
                405                 410

<210> SEQ ID NO 9
<211> LENGTH: 1605
<212> TYPE: DNA
<213> ORGANISM: Pichia Pastoris

<400> SEQUENCE: 9
```

| | | | | | |
|---|---|---|---|---|---|
| atgaaatcgg | ttatttggag | ccttctatct | ttgctagcat | tgtcgcaggc | attgactatt | 60 |
| ccattgctgg | aagagcttca | acagcaaaca | tttttagca | agaaaaccgt | tcctcaacaa | 120 |
| gttgctgaat | tggtgggcac | ccattactct | aaggatgaga | taatcagtct | atggaaggac | 180 |
| attgagctgt | atgtacccag | ggaaaagatc | caagaggcct | tcgataagtt | cgtaaaacaa | 240 |
| tcaactgcca | cttcccccgt | tagaaatgaa | tttcccttgt | ctcagcaaga | ttgggtgaca | 300 |
| gtgaccaaca | ccaagtttga | taattatcaa | ttgagggtta | aaaaatccca | ccctgaaaag | 360 |
| ctaaacattg | ataaggtaaa | gcaatcttcg | ggatacctgg | atatcattga | tcaagataag | 420 |
| catcttttct | attggttttt | tgaatcccga | aatgatccgt | ccacagaccc | aatcatccta | 480 |
| tggttgaatg | gtggacccgg | ctgctcttct | attacagggt | tgctattcga | aaagattggc | 540 |
| cccagttaca | tcaccaaaga | gattaagccg | aacataatc | cttattcatg | gaacaacaat | 600 |
| gctagtgtta | tcttccttga | gcaaccggtt | ggagtaggat | tttcttactc | ttctaagaaa | 660 |
| gtcggtgata | ctgcaactgc | tgccaaagat | acatatgtgt | ttttggagct | tttcttccaa | 720 |
| aagtttcctc | agttcctgac | ctctaatctg | cacattgctg | gggaatcgta | tgctggccat | 780 |
| tatttgccca | agattgcttc | tgagattgtg | tctcacgcag | acaagacgtt | tgacctttca | 840 |
| ggagtcatga | tcggtaatgg | tcttactgat | cctctaattc | agtataagta | ctatcagcca | 900 |
| atggcctgtg | aaaaggtgg | ctacaagcag | gtcatttcgg | acgaggaatg | tgatgaattg | 960 |
| gatagggtct | atccaagatg | tgaacgttta | acgcgggcat | gttatgagtt | ccaaaattca | 1020 |
| gttacttgtg | ttccggcaac | actttattgc | gaccaaaagc | tactgaagcc | gtacactgac | 1080 |
| actggcttga | atgtctatga | tattcgtaca | atgtgcgatg | aagggactga | tttgtgttac | 1140 |
| aaagaactgg | aatacgtgga | gaagtacatg | aaccagcctg | aagtgcagga | agccgtgggc | 1200 |
| tctgaagtca | gttcttacaa | aggttgtgac | gatgatgtct | tcttaagatt | tttgtactct | 1260 |
| ggcgatggat | ctaagccttt | ccaccagtat | atcacggatt | tctcaatgc | aagtattccg | 1320 |
| gttctgattt | acgcaggtga | taaagattat | atctgtaatt | ggctaggaaa | ccaagcttgg | 1380 |

```
gtcaatgagc tagaatggaa cttgtctgag gaattccagg caactccgat tcgaccgtgg   1440
ttcactttgg acaataacga ttatgcagga aacgtacaaa cttatggaaa ctttcctttt   1500
ctaagagtat ttgatgctgg tcacatggtt ccttacaatc aaccagtcaa cgcacttgac   1560
atggttgtca gatggacaca cggtgatttc tcatttggtt attaa                  1605

<210> SEQ ID NO 10
<211> LENGTH: 534
<212> TYPE: PRT
<213> ORGANISM: Pichia Pastoris

<400> SEQUENCE: 10

Met Lys Ser Val Ile Trp Ser Leu Leu Ser Leu Ala Leu Ser Gln
1               5                   10                  15

Ala Leu Thr Ile Pro Leu Leu Glu Glu Leu Gln Gln Gln Thr Phe Phe
                20                  25                  30

Ser Lys Lys Thr Val Pro Gln Gln Val Ala Glu Leu Val Gly Thr His
            35                  40                  45

Tyr Ser Lys Asp Glu Ile Ile Ser Leu Trp Lys Asp Ile Glu Leu Asp
        50                  55                  60

Val Pro Arg Glu Lys Ile Gln Glu Ala Phe Asp Lys Phe Val Lys Gln
65                  70                  75                  80

Ser Thr Ala Thr Ser Pro Val Arg Asn Glu Phe Pro Leu Ser Gln Gln
                85                  90                  95

Asp Trp Val Thr Val Thr Asn Thr Lys Phe Asp Asn Tyr Gln Leu Arg
            100                 105                 110

Val Lys Lys Ser His Pro Glu Lys Leu Asn Ile Asp Lys Val Lys Gln
        115                 120                 125

Ser Ser Gly Tyr Leu Asp Ile Ile Asp Gln Asp Lys His Leu Phe Tyr
    130                 135                 140

Trp Phe Phe Glu Ser Arg Asn Asp Pro Ser Thr Asp Pro Ile Ile Leu
145                 150                 155                 160

Trp Leu Asn Gly Gly Pro Gly Cys Ser Ser Ile Thr Gly Leu Leu Phe
                165                 170                 175

Glu Lys Ile Gly Pro Ser Tyr Ile Thr Lys Glu Ile Lys Pro Glu His
            180                 185                 190

Asn Pro Tyr Ser Trp Asn Asn Asn Ala Ser Val Ile Phe Leu Glu Gln
        195                 200                 205

Pro Val Gly Val Gly Phe Ser Tyr Ser Ser Lys Lys Val Gly Asp Thr
    210                 215                 220

Ala Thr Ala Ala Lys Asp Thr Tyr Val Phe Leu Glu Leu Phe Phe Gln
225                 230                 235                 240

Lys Phe Pro Gln Phe Leu Thr Ser Asn Leu His Ile Ala Gly Glu Ser
                245                 250                 255

Tyr Ala Gly His Tyr Leu Pro Lys Ile Ala Ser Glu Ile Val Ser His
            260                 265                 270

Ala Asp Lys Thr Phe Asp Leu Ser Gly Val Met Ile Gly Asn Gly Leu
        275                 280                 285

Thr Asp Pro Leu Ile Gln Tyr Lys Tyr Tyr Gln Pro Met Ala Cys Gly
    290                 295                 300

Lys Gly Gly Tyr Lys Gln Val Ile Ser Asp Glu Glu Cys Asp Glu Leu
305                 310                 315                 320

Asp Arg Val Tyr Pro Arg Cys Glu Arg Leu Thr Arg Ala Cys Tyr Glu
                325                 330                 335
```

Phe Gln Asn Ser Val Thr Cys Val Pro Ala Thr Leu Tyr Cys Asp Gln
            340                 345                 350

Lys Leu Leu Lys Pro Tyr Thr Asp Thr Gly Leu Asn Val Tyr Asp Ile
        355                 360                 365

Arg Thr Met Cys Asp Glu Gly Thr Asp Leu Cys Tyr Lys Glu Leu Glu
    370                 375                 380

Tyr Val Glu Lys Tyr Met Asn Gln Pro Glu Val Gln Glu Ala Val Gly
385                 390                 395                 400

Ser Glu Val Ser Ser Tyr Lys Gly Cys Asp Asp Val Phe Leu Arg
                405                 410                 415

Phe Leu Tyr Ser Gly Asp Gly Ser Lys Pro Phe His Gln Tyr Ile Thr
            420                 425                 430

Asp Val Leu Asn Ala Ser Ile Pro Val Leu Ile Tyr Ala Gly Asp Lys
        435                 440                 445

Asp Tyr Ile Cys Asn Trp Leu Gly Asn Gln Ala Trp Val Asn Glu Leu
    450                 455                 460

Glu Trp Asn Leu Ser Glu Glu Phe Gln Ala Thr Pro Ile Arg Pro Trp
465                 470                 475                 480

Phe Thr Leu Asp Asn Asn Asp Tyr Ala Gly Asn Val Gln Thr Tyr Gly
                485                 490                 495

Asn Phe Ser Phe Leu Arg Val Phe Asp Ala Gly His Met Val Pro Tyr
            500                 505                 510

Asn Gln Pro Val Asn Ala Leu Asp Met Val Val Arg Trp Thr His Gly
        515                 520                 525

Asp Phe Ser Phe Gly Tyr
    530

<210> SEQ ID NO 11
<211> LENGTH: 1356
<212> TYPE: DNA
<213> ORGANISM: Pichia Pastoris

<400> SEQUENCE: 11
atgatattac acacctatat tattctctcg ttattgacta tatttcctaa agctattggt      60
ctgtccttgc agatgccaat ggccttggaa gctagttatg cctcattagt ggagaaagca     120
accctcgctg ttggacaaga aattgatgcc atacaaaagg gtattcagca aggttggttg     180
gaagtagaga caagatttcc aactatagtg tcacagttat cctatagtac tggcccaaaa     240
tttgcgatca agaagaaaga tgcaactttt tgggatttct atgttgaaag tcaagagttg     300
ccaaactacc gaattaatga aaatctgaaa ccaattttca ccccctattc gtggaatggt     360
aatgcttcaa tcatctactt agatcaaccg gtcaatgttg gttttctta ttcttcatca     420 tcggtgagta acactgttgt tgcgggagaa gatgtgtatg catttcttca gcttttttt      480 caacacttcc cggaatatca aactaatgac tttcatattg ccggtgaatc ttatgcagga     540 cattcattc cggtgtttgc agacgaaatt ttgagtcaaa gaacagaaa tttcaatctt      600 acttcagtct tgatcggaaa tggattaact gaccctttga ctcaataccg atattacgag     660
ccaatggctt gtggtgaagg tggtgcccg tcagtactgc ctgccgatga gtgcgaaaat     720
atgctagtta cccaagataa atgtttgtct ttaattcaag catgctacga ctcacagtcg     780
gcattcacat gcgcaccggc tgccatttat tgtaataacg ctcagatggg accctatcag     840
agaactggga gaatgtgta tgatattcgt aaggaatgtg atggtggatc cttgtgctat     900
aaggaccttg aattcatcga tacctactta aatcaaaagt ttgttcaaga tgctttgggc     960

```
gccgaggtcg ataccatga atcttgcaat tttgaaatca acagaaactt tttatttgct    1020
ggagattgga tgaaaccta tcatgaacat gtcagcagtc tcttgaacaa aggttttgccc   1080 gttttgattt acgcagggga caaagatttc atttgcaact ggttgggtaa tcgagcatgg   1140
actgatgtct tgccgtgggt tgatgctgat ggttttgaaa agccgaagt ccaagattgg    1200 ttggttaatg aaggaaggc tggtgaattt aagaactata gcaacttcac ctacctaagg    1260
gtttatgatg ctggtcatat ggccccatat gatcagccag agaattctca tgaaatggtc   1320
aatagatgga tatccggaga ctttagcttt cactag                             1356
```

<210> SEQ ID NO 12
<211> LENGTH: 451
<212> TYPE: PRT
<213> ORGANISM: Pichia Pastoris

<400> SEQUENCE: 12

```
Met Ile Leu His Thr Tyr Ile Ile Leu Ser Leu Leu Thr Ile Phe Pro
1               5                   10                  15

Lys Ala Ile Gly Leu Ser Leu Gln Met Pro Met Ala Leu Glu Ala Ser
            20                  25                  30

Tyr Ala Ser Leu Val Glu Lys Ala Thr Leu Ala Val Gly Gln Glu Ile
        35                  40                  45

Asp Ala Ile Gln Lys Gly Ile Gln Gln Gly Trp Leu Glu Val Glu Thr
    50                  55                  60

Arg Phe Pro Thr Ile Val Ser Gln Leu Ser Tyr Ser Thr Gly Pro Lys
65                  70                  75                  80

Phe Ala Ile Lys Lys Lys Asp Ala Thr Phe Trp Asp Phe Tyr Val Glu
                85                  90                  95

Ser Gln Glu Leu Pro Asn Tyr Arg Ile Asn Glu Asn Leu Lys Pro Ile
            100                 105                 110

Phe Asn Pro Tyr Ser Trp Asn Gly Asn Ala Ser Ile Ile Tyr Leu Asp
        115                 120                 125

Gln Pro Val Asn Val Gly Phe Ser Tyr Ser Ser Ser Val Ser Asn
    130                 135                 140

Thr Val Val Ala Gly Glu Asp Val Tyr Ala Phe Leu Gln Leu Phe Phe
145                 150                 155                 160

Gln His Phe Pro Glu Tyr Gln Thr Asn Asp Phe His Ile Ala Gly Glu
                165                 170                 175

Ser Tyr Ala Gly His Tyr Ile Pro Val Phe Ala Asp Glu Ile Leu Ser
            180                 185                 190

Gln Lys Asn Arg Asn Phe Asn Leu Thr Ser Val Leu Ile Gly Asn Gly
        195                 200                 205

Leu Thr Asp Pro Leu Thr Gln Tyr Arg Tyr Tyr Glu Pro Met Ala Cys
    210                 215                 220

Gly Glu Gly Gly Ala Pro Ser Val Leu Pro Ala Asp Glu Cys Glu Asn
225                 230                 235                 240

Met Leu Val Thr Gln Asp Lys Cys Leu Ser Leu Ile Gln Ala Cys Tyr
                245                 250                 255

Asp Ser Gln Ser Ala Phe Thr Cys Ala Pro Ala Ile Tyr Cys Asn
            260                 265                 270

Asn Ala Gln Met Gly Pro Tyr Gln Arg Thr Gly Lys Asn Val Tyr Asp
        275                 280                 285

Ile Arg Lys Glu Cys Asp Gly Gly Ser Leu Cys Tyr Lys Asp Leu Glu
    290                 295                 300
```

```
Phe Ile Asp Thr Tyr Leu Asn Gln Lys Phe Val Gln Asp Ala Leu Gly
305                 310                 315                 320

Ala Glu Val Asp Thr Tyr Glu Ser Cys Asn Phe Glu Ile Asn Arg Asn
            325                 330                 335

Phe Leu Phe Ala Gly Asp Trp Met Lys Pro Tyr His Glu His Val Ser
        340                 345                 350

Ser Leu Leu Asn Lys Gly Leu Pro Val Leu Ile Tyr Ala Gly Asp Lys
    355                 360                 365

Asp Phe Ile Cys Asn Trp Leu Gly Asn Arg Ala Trp Thr Asp Val Leu
370                 375                 380

Pro Trp Val Asp Ala Asp Gly Phe Glu Lys Ala Glu Val Gln Asp Trp
385                 390                 395                 400

Leu Val Asn Gly Arg Lys Ala Gly Glu Phe Lys Asn Tyr Ser Asn Phe
                405                 410                 415

Thr Tyr Leu Arg Val Tyr Asp Ala Gly His Met Ala Pro Tyr Asp Gln
            420                 425                 430

Pro Glu Asn Ser His Glu Met Val Asn Arg Trp Ile Ser Gly Asp Phe
        435                 440                 445

Ser Phe His
    450
```

<210> SEQ ID NO 13
<211> LENGTH: 1680
<212> TYPE: DNA
<213> ORGANISM: Pichia Pastoris

<400> SEQUENCE: 13

```
atgcaattgc gtcattccgt tggattggct atcttatctg ccatagcagt ccaaggattg      60
ctaattccta acattgagtc attacccagc cagtttggtg ctaatggtga cagtgaacaa     120
ggtgtattag cccaccatgg taaacatcct aaagttgata tggctcacca tggaaagcat     180
cctaaaatcg ctaaggattc caagggacac cctaagcttt gccctgaagc tttgaagaag     240
atgaaagaag gccacccttc ggctccagtc attactaccc attccgcttc taaaaactta     300
atcccttact cttatattat agtcttcaag aagggtgtca cttcagagga tatcgacttc     360
caccgtgacc ttatctccac tcttcatgaa gagtctgtga gcaaattaag agagtcagat     420
ccaaatcact cattttcgt ttctaatgag aatggcgaaa caggttacac cggtgacttc     480
tccgttggtg acttgctcaa gggttacacc ggatacttca cggatgacac tttagagctt     540
atcagtaagc atccagcagt tgctttcatt gaaagggatt cgagagtatt gccaccgat      600
tttgaaactc aaaacggtgc tccttggggt ttggccagag tctctcacag aaagcctctt     660
tccctaggca gcttcaacaa gtacttatat gatggagctg tggtgaagg tgttacttcc      720
tatgttatcg atacaggtat ccacgtcact cacaaagaat ccagggtag agcatcttgg      780
ggtaagacca ttccagctgg agacgttgat gacgatggaa acggtcacgg aactcactgt     840
gctggtacca ttgcttctga aagctacggt gttgccaaga aggctaatgt tgttgccatc     900
aaggtcttga gatctaatgg ttctggttcg atgtcagatg ttctgaaggg tgttgagtat     960
gccacccaat cccacttgga tgctgttaaa aagggcaaca gaaatttaa gggctctacc     1020
gctaacatgt cactgggtgg tggtaaatct cctgctttgg accttgcagt caatgctgct    1080
gttaagaatg gtattcactt tgccgttgca gcaggtaacg aaaaccaaga tgcttgtaac    1140
acctcgccag cagctgctga gaatgccatc accgtcggtg catcaacctt atcagacgct    1200
```

```
agagcttact tttctaacta cggtaaatgt gttgacattt tcgctccagg tttaaacatt    1260
ctttctacct acactggttc ggatgacgca actgctacct tgtctggtac ttcaatggcc    1320
tctcctcaca ttgctggtct gttgacttac ttcctatcat gcagcctgc tgctggatct     1380 ctgtactcta acggaggatc tgagggtgtc acacctgctc aattgaaaaa gaacctcctc    1440
aagtatgcat ctgtcggagt attagaggat gttccagaag acactccaaa cctcttggtt    1500
tacaatggtg gtggacaaaa cctttcttct ttctggggaa aggagacaga agacaatgtt    1560
gcttcctccg acgatactgg tgagtttcac tcttttgtga acaagcttga atcagctgtt    1620
gaaaacttgg cccaagagtt tgcacattca gtgaaggagc tggcttctga acttatttag   1680
```

<210> SEQ ID NO 14
<211> LENGTH: 559
<212> TYPE: PRT
<213> ORGANISM: Pichia Pastoris

<400> SEQUENCE: 14

```
Met Gln Leu Arg His Ser Val Gly Leu Ala Ile Leu Ser Ala Ile Ala
1               5                   10                  15

Val Gln Gly Leu Leu Ile Pro Asn Ile Glu Ser Leu Pro Ser Gln Phe
            20                  25                  30

Gly Ala Asn Gly Asp Ser Glu Gln Gly Val Leu Ala His His Gly Lys
        35                  40                  45

His Pro Lys Val Asp Met Ala His His Gly Lys His Pro Lys Ile Ala
    50                  55                  60

Lys Asp Ser Lys Gly His Pro Lys Leu Cys Pro Glu Ala Leu Lys Lys
65                  70                  75                  80

Met Lys Glu Gly His Pro Ser Ala Pro Val Ile Thr Thr His Ser Ala
                85                  90                  95

Ser Lys Asn Leu Ile Pro Tyr Ser Tyr Ile Ile Val Phe Lys Lys Gly
            100                 105                 110

Val Thr Ser Glu Asp Ile Asp Phe His Arg Asp Leu Ile Ser Thr Leu
        115                 120                 125

His Glu Glu Ser Val Ser Lys Leu Arg Glu Ser Asp Pro Asn His Ser
    130                 135                 140

Phe Phe Val Ser Asn Glu Asn Gly Glu Thr Gly Tyr Thr Gly Asp Phe
145                 150                 155                 160

Ser Val Gly Asp Leu Leu Lys Gly Tyr Thr Gly Tyr Phe Thr Asp Asp
                165                 170                 175

Thr Leu Glu Leu Ile Ser Lys His Pro Ala Val Ala Phe Ile Glu Arg
            180                 185                 190

Asp Ser Arg Val Phe Ala Thr Asp Phe Glu Thr Gln Asn Gly Ala Pro
        195                 200                 205

Trp Gly Leu Ala Arg Val Ser His Arg Lys Pro Leu Ser Leu Gly Ser
    210                 215                 220

Phe Asn Lys Tyr Leu Tyr Asp Gly Ala Gly Glu Gly Val Thr Ser
225                 230                 235                 240

Tyr Val Ile Asp Thr Gly Ile His Val Thr His Lys Glu Phe Gln Gly
                245                 250                 255

Arg Ala Ser Trp Gly Lys Thr Ile Pro Ala Gly Asp Val Asp Asp
            260                 265                 270

Gly Asn Gly His Gly Thr His Cys Ala Gly Thr Ile Ala Ser Glu Ser
        275                 280                 285

Tyr Gly Val Ala Lys Lys Ala Asn Val Val Ala Ile Lys Val Leu Arg
```

```
            290                 295                 300
Ser Asn Gly Ser Gly Ser Met Ser Asp Val Leu Lys Gly Val Glu Tyr
305                 310                 315                 320

Ala Thr Gln Ser His Leu Asp Ala Val Lys Lys Gly Asn Lys Lys Phe
                325                 330                 335

Lys Gly Ser Thr Ala Asn Met Ser Leu Gly Gly Lys Ser Pro Ala
                340                 345                 350

Leu Asp Leu Ala Val Asn Ala Ala Val Lys Asn Gly Ile His Phe Ala
                355                 360                 365

Val Ala Ala Gly Asn Glu Asn Gln Asp Ala Cys Asn Thr Ser Pro Ala
        370                 375                 380

Ala Glu Asn Ala Ile Thr Val Gly Ala Ser Thr Leu Ser Asp Ala
385                 390                 395                 400

Arg Ala Tyr Phe Ser Asn Tyr Gly Lys Cys Val Asp Ile Phe Ala Pro
                405                 410                 415

Gly Leu Asn Ile Leu Ser Thr Tyr Thr Gly Ser Asp Asp Ala Thr Ala
                420                 425                 430

Thr Leu Ser Gly Thr Ser Met Ala Ser Pro His Ile Ala Gly Leu Leu
                435                 440                 445

Thr Tyr Phe Leu Ser Leu Gln Pro Ala Ala Gly Ser Leu Tyr Ser Asn
        450                 455                 460

Gly Gly Ser Glu Gly Val Thr Pro Ala Gln Leu Lys Lys Asn Leu Leu
465                 470                 475                 480

Lys Tyr Ala Ser Val Gly Val Leu Glu Asp Val Pro Glu Asp Thr Pro
                485                 490                 495

Asn Leu Leu Val Tyr Asn Gly Gly Gln Asn Leu Ser Ser Phe Trp
                500                 505                 510

Gly Lys Glu Thr Glu Asp Asn Val Ala Ser Ser Asp Thr Gly Glu
                515                 520                 525

Phe His Ser Phe Val Asn Lys Leu Glu Ser Ala Val Glu Asn Leu Ala
        530                 535                 540

Gln Glu Phe Ala His Ser Val Lys Glu Leu Ala Ser Glu Leu Ile
545                 550                 555

<210> SEQ ID NO 15
<211> LENGTH: 865
<212> TYPE: PRT
<213> ORGANISM: Pichia Pastoris

<400> SEQUENCE: 15

Met Phe Leu Lys Ser Leu Leu Ser Phe Ala Ser Ile Leu Thr Leu Cys
1               5                   10                  15

Lys Ala Trp Asp Leu Glu Asp Val Gln Asp Ala Pro Lys Ile Lys Gly
                20                  25                  30

Asn Glu Val Pro Gly Arg Tyr Ile Ile Glu Tyr Glu Glu Ala Ser Thr
            35                  40                  45

Ser Ala Phe Ala Thr Gln Leu Arg Ala Gly Gly Tyr Asp Phe Asn Ile
        50                  55                  60

Gln Tyr Asp Tyr Ser Thr Gly Ser Leu Phe Asn Gly Ala Ser Val Gln
65                  70                  75                  80

Ile Ser Asn Asp Asn Lys Thr Thr Phe Gln Asp Leu Gln Ser Leu Arg
                85                  90                  95

Ala Val Lys Asn Val Tyr Pro Ala Thr Leu Ile Thr Leu Asp Glu Thr
                100                 105                 110
```

-continued

```
Phe Glu Leu Ala Asp Thr Lys Pro Trp Asn Pro His Gly Ile Thr Gly
            115                 120                 125

Val Asp Ser Leu His Glu Gln Gly Tyr Thr Gly Ser Gly Val Val Ile
130                 135                 140

Ala Val Ile Asp Thr Gly Val Asp Tyr Thr His Pro Ala Leu Gly Gly
145                 150                 155                 160

Gly Ile Gly Asp Asn Phe Pro Ile Lys Ala Gly Tyr Asp Leu Ser Ser
                165                 170                 175

Gly Asp Gly Val Ile Thr Asn Asp Pro Met Asp Cys Asp Gly His Gly
            180                 185                 190

Thr Phe Val Ser Ser Ile Ile Val Ala Asn Asn Lys Asp Met Val Gly
            195                 200                 205

Val Ala Pro Asp Ala Gln Ile Val Met Tyr Lys Val Phe Pro Cys Ser
210                 215                 220

Asp Ser Thr Ser Thr Asp Ile Val Met Ala Gly Met Gln Lys Ala Tyr
225                 230                 235                 240

Asp Asp Gly His Lys Ile Ile Ser Leu Ser Leu Gly Ser Asp Ser Gly
                245                 250                 255

Phe Ser Ser Thr Pro Ala Ser Leu Met Ala Ser Arg Ile Ala Gln Asp
            260                 265                 270

Arg Val Val Leu Val Ala Ala Gly Asn Ser Gly Glu Leu Gly Pro Phe
            275                 280                 285

Tyr Ala Ser Ser Pro Ala Ser Gly Lys Gln Val Ile Ser Val Gly Ser
            290                 295                 300

Val Gln Asn Glu Gln Trp Thr Thr Phe Pro Val Thr Phe Thr Ser Ser
305                 310                 315                 320

Asn Gly Glu Ser Arg Val Phe Pro Tyr Leu Ala Tyr Asn Gly Ala Gln
                325                 330                 335

Ile Gly Phe Asp Ala Glu Leu Glu Val Asp Phe Thr Glu Glu Arg Gly
            340                 345                 350

Cys Val Tyr Glu Pro Glu Ile Ser Ala Asp Asn Ala Asn Lys Ala Ile
            355                 360                 365

Leu Leu Arg Arg Gly Val Gly Cys Val Glu Asn Leu Glu Phe Asn Leu
            370                 375                 380

Leu Ser Val Ala Gly Tyr Lys Ala Tyr Phe Leu Tyr Asn Ser Phe Ser
385                 390                 395                 400

Arg Pro Trp Ser Leu Leu Asn Ile Ser Pro Leu Ile Glu Leu Asp Asn
                405                 410                 415

Ala Tyr Ser Leu Val Glu Glu Val Gly Ile Trp Val Lys Thr Gln
            420                 425                 430

Ile Asp Ala Gly Asn Thr Val Lys Leu Lys Val Ser Thr Ser Asp Gln
            435                 440                 445

Met Leu Pro Ser Asp Lys Glu Tyr Leu Gly Val Gly Lys Met Asp Tyr
            450                 455                 460

Tyr Ser Ser Gln Gly Pro Ala Tyr Glu Leu Glu Phe Phe Pro Thr Ile
465                 470                 475                 480

Ser Ala Pro Gly Gly Asp Ser Trp Gly Ala Trp Pro Gly Gly Gln Tyr
            485                 490                 495

Gly Val Ala Ser Gly Thr Ser Phe Ala Cys Pro Tyr Val Ala Gly Leu
            500                 505                 510

Thr Ala Leu Tyr Glu Ser Gln Phe Gly Ile Gln Asp Pro Gln Asp Tyr
            515                 520                 525

Val Arg Lys Leu Val Ser Thr Ala Thr Asp Leu Gln Leu Phe Asp Trp
```

-continued

```
    530                 535                 540

Asn Ala Val Lys Leu Glu Thr Ser Met Asn Ala Pro Leu Ile Gln Gln
545                 550                 555                 560

Gly Ala Gly Leu Val Asn Ala Leu Gly Leu Phe Glu Thr Lys Thr Val
                565                 570                 575

Ile Val Ser Ala Pro Tyr Leu Glu Leu Asn Asp Thr Ile Asn Arg Ala
            580                 585                 590

Ser Glu Tyr Thr Ile Gln Ile Lys Asn Glu Asn Ser Glu Thr Ile Thr
        595                 600                 605

Tyr Gln Val Val His Val Pro Gly Thr Thr Val Tyr Ser Arg Ser Ala
    610                 615                 620

Ser Gly Asn Ile Pro Tyr Leu Val Asn Gln Asp Phe Ala Pro Tyr Gly
625                 630                 635                 640

Asp Ser Asp Ala Ala Thr Val Ala Leu Ser Thr Glu Glu Leu Val Leu
                645                 650                 655

Gly Pro Gly Glu Val Gly Glu Val Thr Val Ile Phe Ser Thr Glu Glu
            660                 665                 670

Ile Asp Gln Glu Thr Ala Pro Ile Ile Gln Gly Lys Ile Thr Phe Tyr
        675                 680                 685

Gly Asp Val Ile Pro Ile Ala Val Pro Tyr Met Gly Val Glu Val Asp
    690                 695                 700

Ile His Ser Trp Glu Pro Leu Ile Glu Arg Pro Leu Ser Val Arg Met
705                 710                 715                 720

Tyr Leu Asp Asp Gly Ser Leu Ala Tyr Val Asp Asp Asp Pro Asp Tyr
                725                 730                 735

Glu Phe Asn Val Tyr Asp Trp Asp Ser Pro Arg Phe Tyr Phe Asn Leu
            740                 745                 750

Arg Tyr Ala Thr Lys Glu Val Ser Ile Asp Leu Val His Pro Asp Tyr
        755                 760                 765

Ser Ile Glu Asn Asp Tyr Glu Trp Pro Leu Val Ser Gly His Asn Asn
    770                 775                 780

Tyr Tyr Gly Pro Val Gly Tyr Asp Tyr Asp Tyr Thr Ser Gly Gln Ala
785                 790                 795                 800

Phe Leu Pro Arg Tyr Phe Gln Gln Arg Ile Asn Glu Leu Gly Tyr Leu
                805                 810                 815

Ser Phe Ser Arg Phe Ala Asn Phe Ser Val Val Pro Ala Gly Glu Tyr
            820                 825                 830

Lys Ala Leu Phe Arg Val Leu Leu Pro Tyr Gly Asp Phe Trp Asn Lys
        835                 840                 845

Glu Asp Trp Gln Leu Phe Glu Ser Pro Val Phe Asn Val Leu Ala Phe
    850                 855                 860

Phe
865
```